US012139476B2

(12) United States Patent
Wang et al.

(10) Patent No.: US 12,139,476 B2
(45) Date of Patent: *Nov. 12, 2024

(54) 3-ARYLOXYL-3-FIVE-MEMBERED HETEROARYL PROPYLAMINE COMPOUND AND USE THEREOF

(71) Applicant: Shanghai Leado Pharmatech Co. Ltd., Shanghai (CN)

(72) Inventors: Youxin Wang, Shanghai (CN); Lingling Zhang, Shanghai (CN)

(73) Assignee: SHANGHAI LEADO PHARMATECH CO. LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/268,914

(22) PCT Filed: Aug. 15, 2019

(86) PCT No.: PCT/CN2019/100846
§ 371 (c)(1),
(2) Date: Feb. 17, 2021

(87) PCT Pub. No.: WO2020/035040
PCT Pub. Date: Feb. 20, 2020

(65) Prior Publication Data
US 2021/0332035 A1 Oct. 28, 2021

(30) Foreign Application Priority Data

Aug. 17, 2018 (CN) .......... 201810942562.6
May 16, 2019 (CN) .......... 201910411311.X

(51) Int. Cl.
*C07D 409/12* (2006.01)
*C07D 333/20* (2006.01)
*C07D 407/12* (2006.01)

(52) U.S. Cl.
CPC ......... *C07D 409/12* (2013.01); *C07D 333/20* (2013.01); *C07D 407/12* (2013.01)

(58) Field of Classification Search
CPC .................................................. C07D 409/12
See application file for complete search history.

(56) References Cited

U.S. PATENT DOCUMENTS

| 5,023,269 | A | 6/1991 | Robertson et al. |
| 7,037,932 | B2* | 5/2006 | Gallagher .......... C07D 333/68 514/415 |
| 2011/0178127 | A1 | 7/2011 | Zhong et al. |
| 2017/0369466 | A1 | 12/2017 | Guo et al. |
| 2019/0175599 | A1 | 6/2019 | Khairatkar-Joshi et al. |
| 2021/0332035 | A1 | 10/2021 | Wang et al. |
| 2022/0119375 | A1 | 4/2022 | Wang et al. |

FOREIGN PATENT DOCUMENTS

| CN | 101657438 A | 2/2010 |
| CN | 105497019 A | 4/2016 |
| CN | 105497020 A | 4/2016 |
| CN | 107625762 A | 1/2018 |
| CN | 107840845 A | 3/2018 |
| CN | 108947989 A | 12/2018 |
| CN | 109748914 A | 5/2019 |
| CN | 111943943 A | 11/2020 |
| CN | 107151241 B | 12/2020 |
| EP | 0273658 A1 | 7/1988 |
| EP | 2305669 A1 | 4/2011 |
| EP | 3339304 A1 | 6/2018 |
| JP | 2004534037 A | 11/2004 |
| JP | 2011525497 A | 9/2011 |
| WO | 02094262 A1 | 11/2002 |
| WO | 2007005644 A2 | 1/2007 |
| WO | 2011060962 A1 | 5/2011 |
| WO | 2011128370 A1 | 10/2011 |
| WO | 2014096377 A1 | 6/2014 |
| WO | 2018115064 A1 | 6/2018 |
| WO | 2018115069 A1 | 6/2018 |
| WO | 2020035070 A1 | 2/2020 |
| WO | 2020228789 A1 | 11/2020 |
| WO | 2021160134 A1 | 8/2021 |
| WO | 2023016249 A1 | 2/2023 |

OTHER PUBLICATIONS

Banker, G.S. "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Rautio "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Malmborg "Predicting human exposure of active drug after oral prodrug administration, using a joined in vitro/in silico-in vivo extrapolation and physiologically-based pharmacokinetic modeling approach" Journal of Pharmacological and Toxicological Methods 67 (2013) 203-213.*
Bymaster, "Duloxetine (CymbaltaTM), a Dual Inhibitor of Serotonin and Norepinephrine Reuptake" Bioorganic and Medicinal Chemistry Letters 2003, 13, 4477.*
Ding "TRPA1 channel mediates organophosphate-induced delayed neuropathy" Cell Discovery (2017) 3, 17024.*

(Continued)

*Primary Examiner* — David K O'Dell
(74) *Attorney, Agent, or Firm* — Panitch Schwarze Belisario & Nadel LLP

(57) ABSTRACT

Disclosed are a 3-aryloxyl-3-five-membered heteroaryl propylamine compound and use thereof. Specifically disclosed is a compound or a pharmacologically acceptable salt thereof or a prodrug thereof. The compound has the structure of formula I. The compound or the pharmacologically acceptable salt thereof or the prodrug thereof has excellent inhibition to transient receptor potential (TPR) channel proteins, and has good therapeutic effect on diseases related to the TPR channel proteins.

12 Claims, 3 Drawing Sheets

(56) References Cited

OTHER PUBLICATIONS

Gleeson, M.P., Hersey, A., Montanari, D. & Overington, J. Probing the links between in vitro potency, ADMET and physicochemical parameters. Nat. Rev. Drug Discov. 10, 197-208 (2011).*

Morrison, K. "Physical Science Level 3" Pearson Education: Capetown, 2008, pp. 16-18.*

Int'l Search Report issued Nov. 19, 2019 in Int'l Application No. PCT/CN2019/101197.

Boot et al, "Benzothienyloxy phenylpropanamines, novel dual inhibitors of serotonin and norepinephrine reuptake," Bioorganic & Medicinal Chemistry Letters, vol. 14, pp. 5395-5399 (Sep. 2004).

Cashman et al, "Inhibition of serotonin and norepinephrine reuptake and inhibition of phosphodiesterase by multi-target inhibitors as potential agents for depression," Bioorganic & Medicinal Chemistry, vol. 17, pp. 6890-6897 (Aug. 2009).

Int'l Search Report issued Nov. 13, 2019 in Int'l Application No. PCT/CN2019/100846.

Zhang et al, "Design, Synthesis and Antidepressive Activity of Duloxetine Derivatives," Acta Pharmaceutica Sinica, vol. 45, No. 7, pp. 869-873 (Dec. 2004).

RN 1181660-13-8 (Sep. 2009).

Extended European Search Report issued Jan. 19, 2022 in EP Application No. 19849600.2.

Extended European Search Report issued Sep. 16, 2021 in EP Application No. 19849974.1.

Office Action issued Apr. 14, 2022 in JP Application No. 2021532506 (Translation Only).

Office Action issued Apr. 14, 2022 in JP Application No. 2021532507 (Translation Only).

Xue et al., "Pharmacokinetic profiles contribute to the differences in behavioral pharmacology of 071031B enantiomers as novel serotonin and norepinephrine reuptake inhibitors," Journal of Psychopharmacology, vol. 31, No. 3, pp. 377-386 (2016).

Zhang, "Analgesic effect and mechanisms of amoxetine as a novel potent serotonin and norepinephrine dual reuptake inhibitor," China Academic Journal Electronic Publishing House, pp. 1-101 (partial English translation at pp. 9-12) (2016).

Office Action issued Nov. 17, 2022 in JP Application No. 2021532507 (English Translation Only).

Science of Kampo Medicine Chinese Medicine, vol. 37, pp. 164-175 (2013) (English abstract).

Wong et al., "Dual serotonin and noradrenaline uptake inhibitor class of antidepressants—Potential for greater efficacy or just hype?," Progress in Drug Research, vol. 58, pp. 169-222 (2002).

Xue et al., "Antidepressant-like effects of 071031B, a novel serotonin and norepinephrine reuptake inhibitor," European Neuropsychopharmacology, vol. 23, pp. 728-741 (2013).

* cited by examiner

3-ARYLOXYL-3-FIVE-MEMBERED HETEROARYL PROPYLAMINE COMPOUND AND USE THEREOF

CROSS-REFERENCE TO RELATED APPLICATIONS

This application is a Section 371 of International Application No. PCT/CN2019/100846, filed Aug. 15, 2019, which was published in the Chinese language on Feb. 20, 2020 under International Publication No. WO 2020/035040 A1, which claims priority under 35 U.S.C. § 119(b) to Chinese Application No. 201810942562.6, filed on Aug. 17, 2018, and Chinese Application No. 201910411311.X, filed on May 16, 2019, the disclosures of which are incorporated herein by reference in their entireties.

FIELD OF THE INVENTION

The present invention relates to the field of medicinal chemistry and pharmacotherapy. Specifically, the present invention relates to a 3-aryloxyl-3-five-membered heteroaryl propylamine compound and use thereof.

BACKGROUND OF THE INVENTION

Pain is known as the fifth vital sign and is a warning sign of body tissues damage. Pain is one of the most common reasons for patients to seek medical treatment. According to the duration time, it is divided into acute pain (which has rapid occurrence, short duration or continuous state) and chronic pain (which has slow occurrence or is transformed from acute pain, has long duration or intermittent occurrence, and no obvious damage can be found for many chronic pains). Acute pain is mostly nociceptive pain caused by tissue trauma, comprising postoperative pain, trauma, post-burn pain, obstetric pain, angina, biliary colic, renal colic and other visceral pain, fracture pain, toothache, cancer pain, etc. Surgery pain and post-traumatic pain are the most common clinical acute pain and the most urgent need for treatment. Chronic pain mainly comprises neuropathic pain, painful osteoarthritis, chronic low back pain and angiogenic pain. Trigeminal neuralgia, diabetic pain, sciatica or post-zoster neuralgia are the main types of neuropathic pain. The global prevalence of neuropathic pain is about 10% with high incidence and large patient population. In the United States, 10%-30% of people suffer from chronic pain, resulting in an annual social expenditure of about 635 billion dollars, which exceeds the total cost of cancer and heart disease. Chronic pain has complex causes and is a refractory disease. Only less than 50% of patients can achieve effective analgesia via drug treatment. It is estimated that the total market scale of neuralgia drugs in China will be close to 26 billion RMB by 2026, and the market scale of ion channel neuropathic pain drugs will exceed 20 billion RMB.

Traditional analgesic drugs mainly comprise opioids and non-steroidal anti-inflammatory drugs. Opioids have strong analgesic effects, but long-term use of opioids can easily lead to tolerance, dependence and addiction, and opioids have adverse effects such as respiratory depression and central sedation, etc. Non-steroidal anti-inflammatory drugs only exert a moderate analgesic effect, but also have adverse effects such as gastrointestinal bleeding and cardiotoxicity, etc. The National Security Council recently released a report on preventable death, showing that the number of death caused by opioid overdose exceeded the number of death caused by car accident for the first time in American history. According to the Commission's analysis of accidental death data in 2017, 1 of 96 Americans died from opioid overdose, and the number of fatalities in a car accident is 1 of 103 Americans. The abuse of opioids has caused severe social crisis in the United States today, so the market needs analgesic drugs with new mechanism.

TRPA1 is a member of the TRP ion channel superfamily and the only member of the TRPA subfamily. It is a non-selective cation channel and is permeable to $Na^+$, $K^+$, $Ca^{2+}$ and $Mg^{2+}$. TRPA1 is mainly distributed on the primary sensory neurons of the dorsal root nerve (DRG), trigeminal nerve (TG) and vagus nerve (VG). From the distribution of the human system, TRPA1 is highly expressed in the peripheral nervous system, respiratory system, gastrointestinal system and urinary system. When these organs and tissues have abnormal functions, the expression and function of TRPA1 channels are usually abnormal simultaneously. TRPA1 can convert cold stimulation, chemical stimulation and mechanical stimulation into inward currents, trigger a series of physiological functions, and participate in the formation of various pain sensations. Inflammatory pain is common problem of certain chronic diseases, and there is still no effective treatment method in the clinic. Animal experimental studies have shown that TRPA1 is involved in inflammatory response and plays an important role in inflammatory pain. The use of TRA1 specific blockers can significantly reduce the inflammatory pain response in rats. From the current research, TRPA1 plays an important role in the occurrence of asthma and cough. Compounds that induce asthma and cough, either cellular endogenous factors or exogenous factors, can activate TRPA1. TRPA1 antagonists can reduce asthma symptoms and block airway hyper-responsiveness. It is confirmed that TRPA1 participates in the regulation of visceral hypersensitivity and plays an important role in visceral pain through different animal models for visceral hypersensitivity, such as colitis, rectal dilation or stress. Neuropathic pain is a pain syndrome caused by central or peripheral nervous system damage or disease, mainly manifested as hyperalgesia, allodynia, and spontaneous pain. In recent years, more and more studies have shown that TRPA1 channels play an important role in different neurogenic pain, such as diabetic neuropathy and neuropathy caused by chemotherapy drugs. Recent studies have also shown that TRPA1 also has a mediating role in toothache, migraine and other pains. The administration of TRPA1 antagonists can significantly alleviate the pain symptoms.

TRPA1 is widely distributed and expressed in the human system. In addition to the physiological functions of TRPA1, the development of TRPA1 inhibitor indications reported so far also involves inflammatory bowel disease, chronic obstructive pulmonary disease, antitussive, antipruritic, allergic rhinitis, ear disease, diabetic, urinary incontinence, etc. TRPA1 is a proven new target for the treatment of many diseases.

Therefore, considering the current unmet clinical needs for pain treatment and the many problems of the existing therapeutic drugs, there is an urgent need in the art to develop therapeutic drug targeting TRP (especially TRPA1) to improve the therapeutic effect of diseases.

SUMMARY OF THE INVENTION

It is an object of the present invention to provide novel compounds which target TRP channel, especially TRPA1, and uses thereof.

In the first aspect of the present invention, it provides a use of a compound, or a pharmaceutically acceptable salt, or a prodrug thereof for (a) preparing a transient receptor potential channel protein (TRPA1) inhibitor; or (b) preparing a medicine for preventing and/or treating a disease related to transient receptor potential channel protein (TRPA1);

wherein the compound has a structure of formula Z:

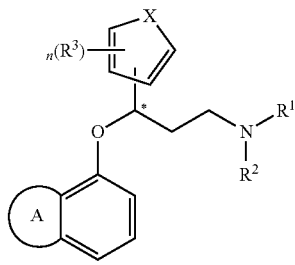

wherein,
ring A is a substituted or unsubstituted 5-7 membered carbocyclic ring, a substituted or unsubstituted 5-7 membered heterocyclic ring, or a substituted or unsubstituted 5-7 membered heteroaromatic ring;
$R^1$ and $R^2$ are each independently hydrogen, substituted or unsubstituted $C_1$-$C_6$ alkyl, or substituted or unsubstituted $C_3$-$C_7$ cycloalkyl;
X is oxygen atom, sulfur atom or nitrogen atom;
$R^3$ is hydrogen, halogen, substituted or unsubstituted $C_1$-$C_6$ alkyl, or substituted or unsubstituted $C_3$-$C_7$ cycloalkyl;
n is 1, 2 or 3;
"*" means that the configuration of the compound is racemate;
wherein any of the "substituted" means that 1-4 (preferably 1, 2, 3, or 4) hydrogen atoms on the group are each independently substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 6-membered aryl or 5- or 6-membered heteroaryl (preferably $C_5$ heteroaryl);
wherein the heterocyclic ring, heteroaromatic ring and heteroaryl each independently have 1 to 3 (preferably 1, 2 or 3) heteroatoms selected from N, O and S.

In another preferred embodiment, A is a substituted or unsubstituted 5-7 membered carbocyclic ring or 5-7 membered heteroaromatic ring.

In another preferred example, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, or substituted or unsubstituted $C_1$-$C_6$ alkyl.

In another preferred embodiment, $R^3$ is hydrogen, halogen, or substituted or unsubstituted $C_1$-$C_4$ alkyl.

In another preferred example, A is a substituted or unsubstituted 5-membered carbocyclic ring, a substituted or unsubstituted 6-membered carbocyclic ring, or a substituted or unsubstituted furan ring.

In another preferred embodiment, $R^1$ and $R^2$ are each independently hydrogen, methyl or ethyl.

In another preferred embodiment, $R^3$ is hydrogen atom, chlorine or a methyl.

In another preferred embodiment, n is 1.

In another preferred embodiment, A is 5-membered carbocyclic ring, 6-membered carbocyclic ring or furan ring.

In another preferred embodiment, n is 1, 2, or 3.

In another preferred embodiment, X is S.

In another preferred embodiment, ring A is furan ring.

In another preferred embodiment, the ring containing X is thiophene ring.

In another preferred embodiment, the structure of the thiophene ring is

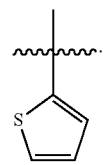 [SMILES: *c1cccs1]

In another preferred embodiment, the structure of phenyl fused with ring A is

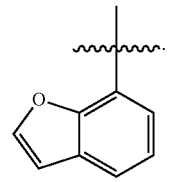 [SMILES: *c1cccc2ccoc12]

In the invention, " ∿∿∿ " is connecting site of a group.

In another preferred embodiment, the compound of formula Z is selected from the following group:

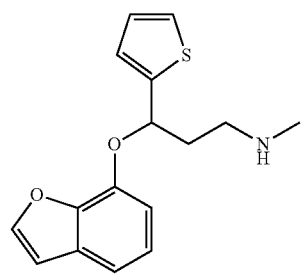

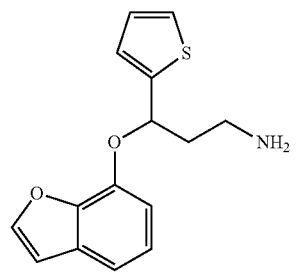

-continued

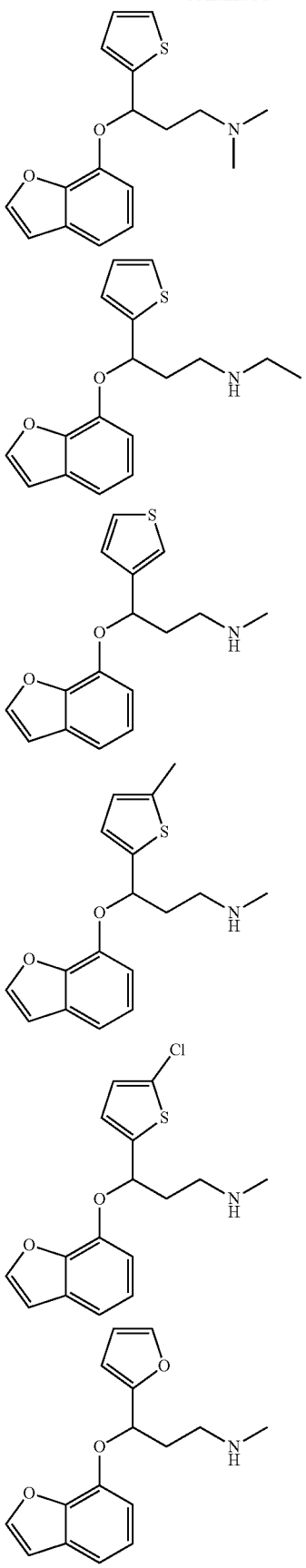

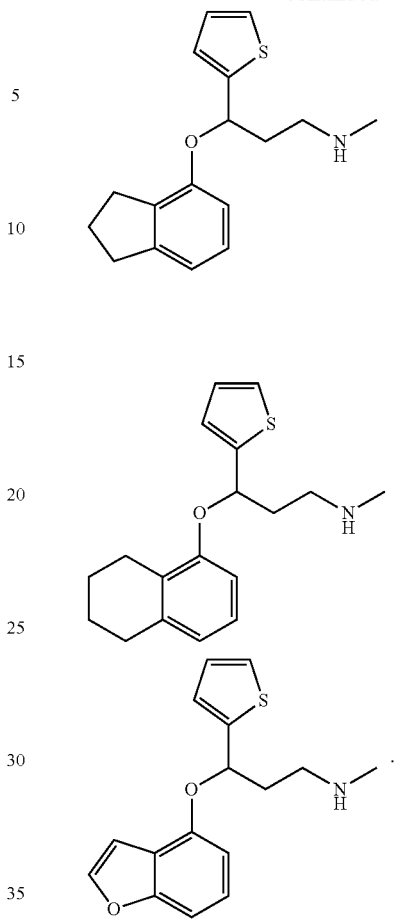

In another preferred embodiment, the disease related to transient receptor potential channel protein (TRPA1) is selected from the group consisting of pain, epilepsy, inflammation, respiratory disorder, pruritus, urinary tract disorder, inflammatory bowel disease, and a combination thereof.

In another preferred embodiment, the pain is selected from the group consisting of acute pain, inflammatory pain, visceral pain, neurogenic pain, muscle fiber pain, headache, neuralgia, mixed pain, cancer-induced pain, and a combination thereof.

In another preferred embodiment, the acute pain is injury pain or postoperative pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscle tension pain.

In another preferred embodiment, the neuralgia is trigeminal neuralgia, diabetic pain, sciatica or post-zoster neuralgia.

In the second aspect of the present invention, it provides a use of a compound, or a pharmaceutically acceptable salt, or a prodrug thereof for (a) preparing a transient receptor potential channel protein (TRP) inhibitor; or (b) preparing a medicine for preventing and/or treating a disease related to transient receptor potential channel protein (TRP);

wherein the compound has a structure of formula I:

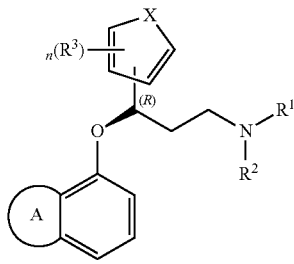

wherein,
Ring A is a substituted or unsubstituted 5-7 membered carbocyclic ring, a substituted or unsubstituted 5-7 membered heterocyclic ring, or a substituted or unsubstituted 5-7 membered heteroaromatic ring;
$R^1$ and $R^2$ are each independently hydrogen, substituted or unsubstituted $C_1$-$C_6$ alkyl, or substituted or unsubstituted $C_3$-$C_7$ cycloalkyl;
X is oxygen atom, sulfur atom or nitrogen atom;
$R^3$ is hydrogen, halogen, substituted or unsubstituted $C_1$-$C_6$ alkyl, or substituted or unsubstituted $C_3$-$C_7$ cycloalkyl;
n is 1, 2 or 3;
wherein any of the "substituted" means that 1-4 (preferably 1, 2, 3, or 4) hydrogen atoms on the group are each independently substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 6-membered aryl or 5- or 6-membered heteroaryl (preferably $C_5$ heteroaryl);
wherein the heterocyclic ring, heteroaromatic ring and heteroaryl each independently have 1 to 3 (preferably 1, 2 or 3) heteroatoms selected from N, O and S.

In another preferred embodiment, A is a substituted or unsubstituted 5-7 membered carbocyclic ring or a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, or substituted or unsubstituted $C_1$-$C_6$ alkyl.

In another preferred embodiment, $R^3$ is hydrogen, halogen, or substituted or unsubstituted $C_1$-$C_4$ alkyl.

In another preferred embodiment, A is a substituted or unsubstituted 5-membered carbocyclic ring, a substituted or unsubstituted 6-membered carbocyclic ring, or a substituted or unsubstituted furan ring.

In another preferred embodiment, $R^1$ and $R^2$ are each independently hydrogen, methyl or ethyl.

In another preferred embodiment, $R^3$ is hydrogen atom, chlorine or a methyl.

In another preferred embodiment, n is 1.

In another preferred embodiment, A is 5-membered carbocyclic ring, 6-membered carbocyclic ring or furan ring.

In another preferred embodiment, n is 1, 2, or 3.

In another preferred embodiment, X is S.

In another preferred embodiment, ring A is furan ring.

In another preferred embodiment, the ring containing X is thiophene ring.

In another preferred embodiment, the structure of the thiophene ring is

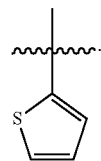

In another preferred embodiment, the structure of phenyl fused with ring A is

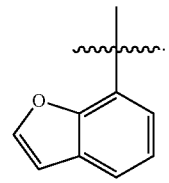 [SMILES: *c1cccc2ccoc12]

In the invention, "〰〰〰" is connecting site of a group.

In another preferred embodiment, the compound is selected from the following group:

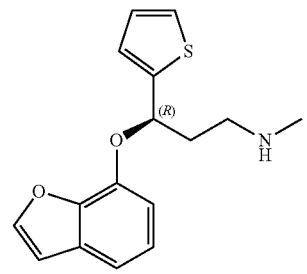

I-1

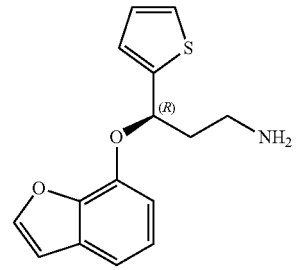

I-2

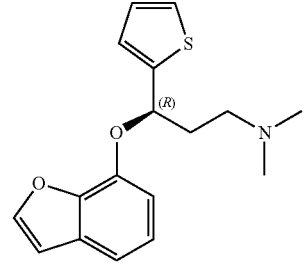

I-3

-continued

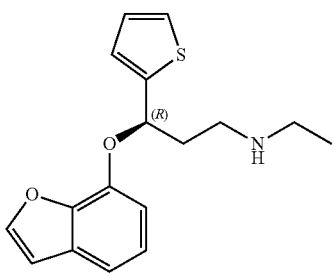
I-4
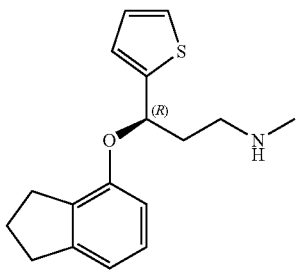
I-9

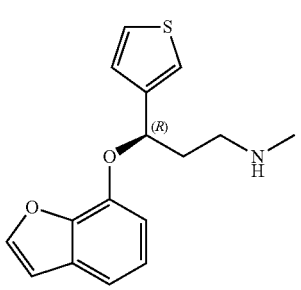
I-5
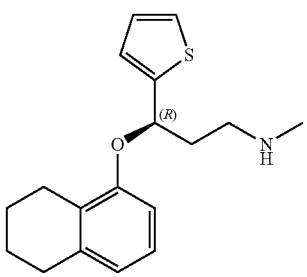
I-10

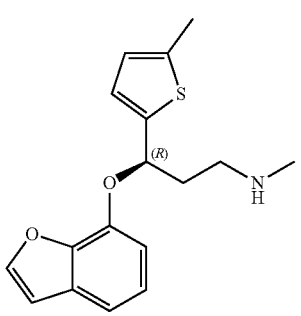
I-6
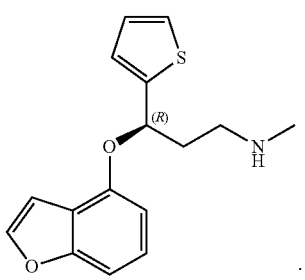
I-11

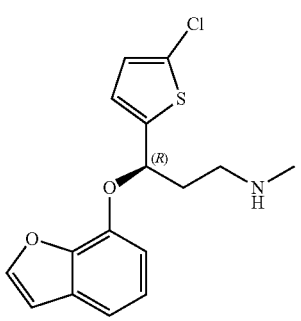
I-7

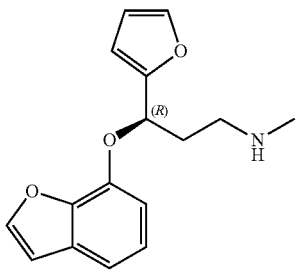
I-8

In another preferred embodiment, the transient receptor potential channel protein (TRP) is TRPA1.

In another preferred embodiment, the disease related to transient receptor potential channel protein (TRPA) is selected from the group consisting of pain, epilepsy, inflammation, respiratory disorder, pruritus, urinary tract disorder, inflammatory bowel disease, and a combination thereof.

In another preferred embodiment, the pain is selected from the group consisting of acute pain, inflammatory pain, visceral pain, neurogenic pain, muscle fiber pain, headache, neuralgia, mixed pain, cancer-induced pain, and a combination thereof.

In another preferred embodiment, the acute pain is injury pain or postoperative pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscle tension pain.

In another preferred embodiment, the neuralgia is trigeminal neuralgia, diabetic pain, sciatica or post-zoster neuralgia.

In the third aspect of the present invention, it provides a compound, or a pharmaceutically acceptable salt, or a prodrug thereof;

wherein the compound has a structure of formula Z:

Z wherein,
Ring A is a substituted or unsubstituted 5-7 membered carbocyclic ring, a substituted or unsubstituted 5-7 membered heterocyclic ring, or a substituted or unsubstituted 5-7 membered heteroaromatic ring;
$R^1$ and $R^2$ are each independently hydrogen, substituted or unsubstituted $C_1$-$C_6$ alkyl, or substituted or unsubstituted $C_3$-$C_7$ cycloalkyl;
X is oxygen atom, sulfur atom or nitrogen atom;
$R^3$ is hydrogen, halogen, substituted or unsubstituted $C_1$-$C_6$ alkyl, or substituted or unsubstituted $C_3$-$C_7$ cycloalkyl;
n is 1, 2 or 3;
"*" means that the configuration of the compound is racemate;
wherein any of the "substituted" means that 1-4 (preferably 1, 2, 3, or 4) hydrogen atoms on the group are each independently substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 6-membered aryl or 5- or 6-membered heteroaryl (preferably $C_5$ heteroaryl);
wherein the heterocyclic ring, heteroaromatic ring and heteroaryl each independently have 1 to 3 (preferably 1, 2 or 3) heteroatoms selected from N, O and S.

In another preferred embodiment, A is a substituted or unsubstituted 5-7 membered carbocyclic ring or a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, or substituted or unsubstituted $C_1$-$C_6$ alkyl.

In another preferred embodiment, $R^3$ is hydrogen, halogen, or substituted or unsubstituted $C_1$-$C_4$ alkyl.

In another preferred embodiment, A is a substituted or unsubstituted 5-membered carbocyclic ring, a substituted or unsubstituted 6-membered carbocyclic ring, or a substituted or unsubstituted furan ring.

In another preferred embodiment, $R^1$ and $R^2$ are each independently hydrogen, methyl or ethyl.

In another preferred embodiment, $R^3$ is hydrogen atom, chlorine or a methyl.

In another preferred embodiment, n is 1.

In another preferred embodiment, A is 5-membered carbocyclic ring, 6-membered carbocyclic ring or furan ring.

In another preferred embodiment, n is 1, 2, or 3.

In another preferred embodiment, X is S.

In another preferred embodiment, ring A is furan ring.

In another preferred embodiment, the ring containing X is thiophene ring.

In another preferred embodiment, the structure of the thiophene ring is

In another preferred embodiment, the structure of phenyl fused with ring A is

In the invention, "〜〜〜" is connecting site of a group.

In another referred embodiment the compound is selected from the following group:

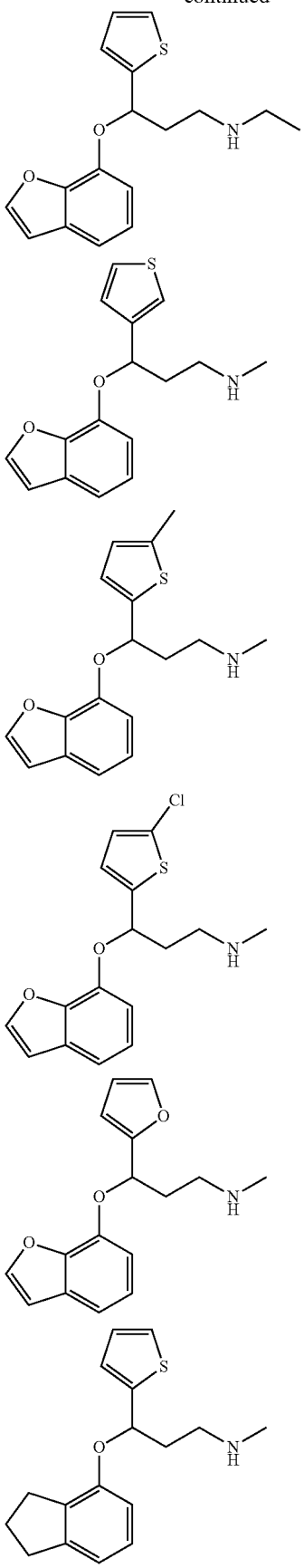

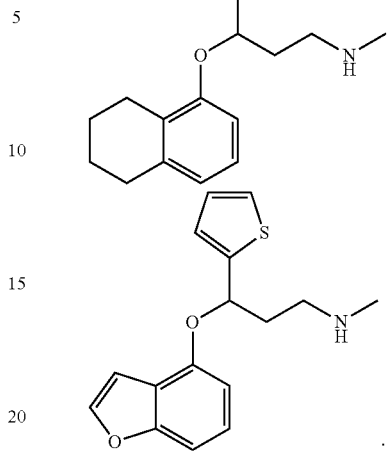

In the fourth aspect of the present invention, it provides a compound, or a pharmaceutically acceptable salt, or a prodrug thereof;
wherein the compound has a structure of formula I:

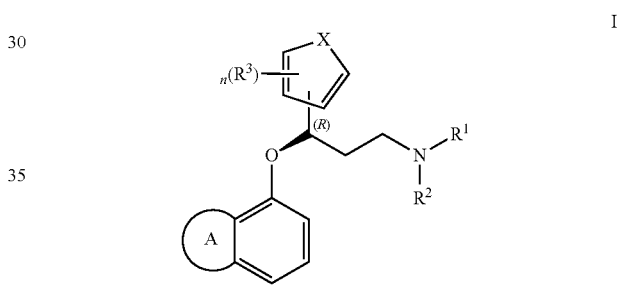

I wherein,
Ring A is a substituted or unsubstituted 5-7 membered carbocyclic ring, a substituted or unsubstituted 5-7 membered heterocyclic ring, or a substituted or unsubstituted 5-7 membered heteroaromatic ring;
$R^1$ and $R^2$ are each independently hydrogen, substituted or unsubstituted $C_1$-$C_6$ alkyl, or substituted or unsubstituted $C_3$-$C_7$ cycloalkyl;
X is oxygen atom, sulfur atom or nitrogen atom;
$R^3$ is hydrogen, halogen, substituted or unsubstituted $C_1$-$C_6$ alkyl, or substituted or unsubstituted $C_3$-$C_7$ cycloalkyl;
n is 1, 2 or 3;
wherein any of the "substituted" means that 1-4 (preferably 1, 2, 3, or 4) hydrogen atoms on the group are each independently substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 6-membered aryl or 5- or 6-membered heteroaryl (preferably $C_5$ heteroaryl);
wherein the heterocyclic ring, heteroaromatic ring and heteroaryl each independently have 1 to 3 (preferably 1, 2 or 3) heteroatoms selected from N, O and S.
In another preferred embodiment, A is a substituted or unsubstituted 5-7 membered carbocyclic ring or a 5-7 membered heteroaromatic ring.

In another preferred embodiment, X is S or O.

In another preferred embodiment, R¹ and R² are each independently hydrogen or substituted or unsubstituted $C_1$-$C_3$ alkyl.

In another preferred embodiment, R³ is hydrogen, halogen, or substituted or unsubstituted $C_1$-$C_6$ alkyl.

In another preferred embodiment, R³ is hydrogen, halogen, or substituted or unsubstituted $C_1$-$C_4$ alkyl.

In another preferred embodiment, A is a substituted or unsubstituted 5-membered carbocyclic ring, a substituted or unsubstituted 6-membered carbocyclic ring, or a substituted or unsubstituted furan ring.

In another preferred embodiment, R¹ and R² are each independently hydrogen, methyl or ethyl.

In another preferred embodiment, R³ is hydrogen atom, chlorine or a methyl.

In another preferred embodiment, n is 1.

In another preferred embodiment, A is 5-membered carbocyclic ring, 6-membered carbocyclic ring or furan ring.

In another preferred embodiment, n is 1, 2, or 3.

In another preferred embodiment, X is S.

In another preferred embodiment, ring A is furan ring.

In another preferred embodiment, the ring containing X is thiophene ring.

In another preferred embodiment, the structure of the thiophene ring is

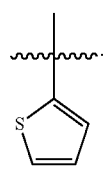

In another preferred embodiment, the structure of phenyl fused with ring A is

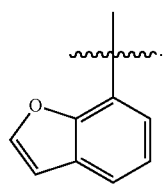 [SMILES: *c1cccc2ccoc12]

In the invention, " ⌇⌇⌇ " is connecting site of a group.

In another preferred embodiment the compound is selected from the following up:

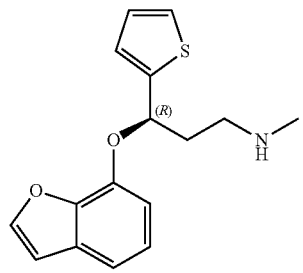

I-1

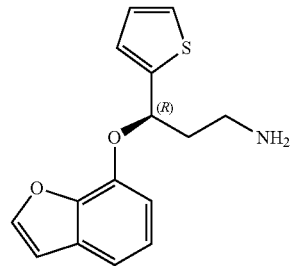

I-2

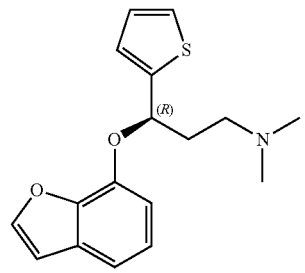

I-3

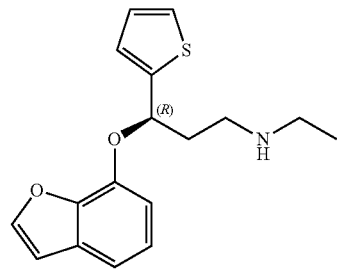

I-4

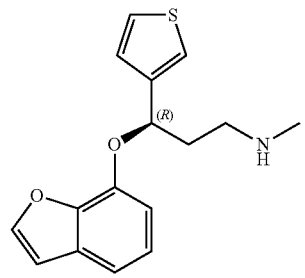

I-5

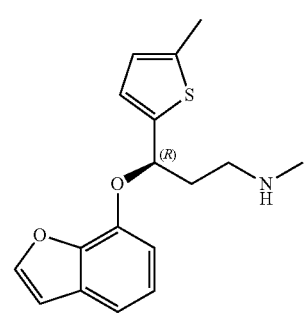

I-6

-continued

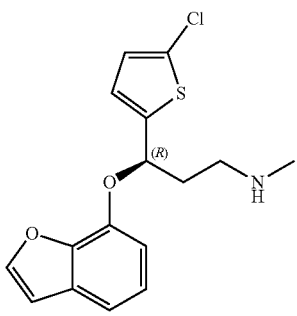
I-7

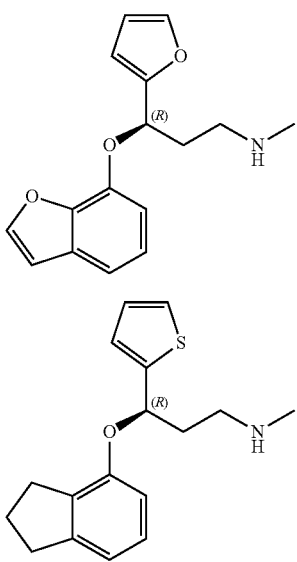
I-8

I-9

I-10

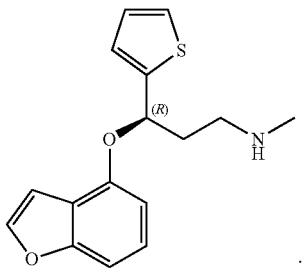
I-11

In the fifth aspect of the present invention, it provides a pharmaceutical composition, which comprises the compound, or a pharmaceutically acceptable salt, or a prodrug thereof according to the third and/or fourth aspect of the present invention; and a pharmaceutically acceptable carrier.

In the sixth aspect of the present invention, it provides a method for preparing the compound, or a pharmaceutically acceptable salt, or a prodrug thereof according to the fourth aspect of the present invention, wherein the method comprises: in an inert solvent, reacting an intermediate of formula II with $R^1$—NH—$R^2$, thereby forming the compound:

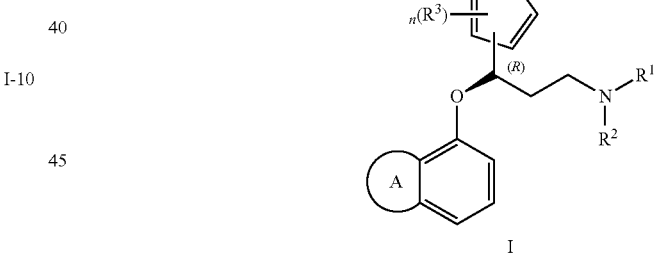

wherein X, A, $R^1$, $R^2$, $R^3$ and n are as defined in the fourth aspect of the present invention.

In another preferred embodiment, the method comprises the following step:

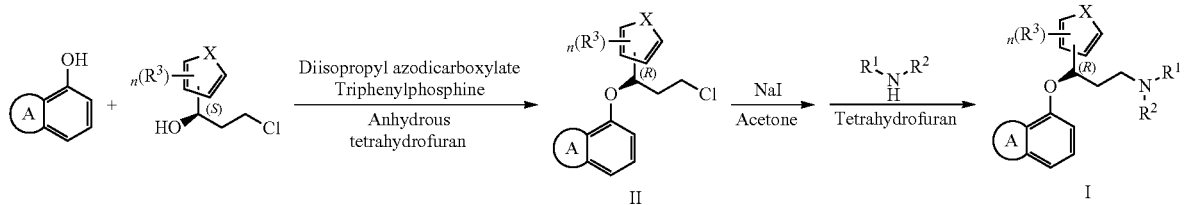

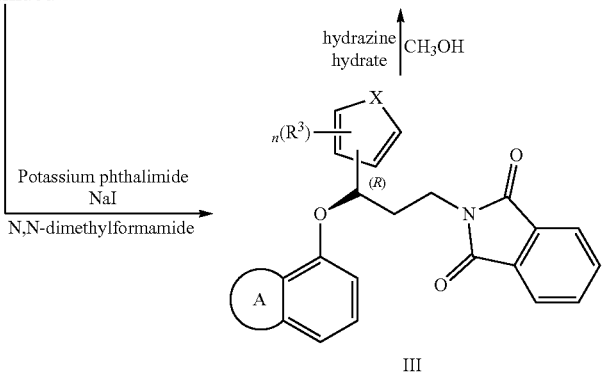

wherein X, A, $R^1$, $R^2$, $R^3$ and n are as defined in the fourth aspect of the present invention;
(a) in an inert solvent and in presence of a condensing agent, reacting a compound of

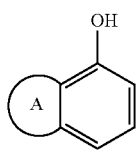

with (S)-1-(($R^3$)n-five-membered heteroaryl)-3-chloropropanol, thereby forming an intermediate of formula II;
(b) carrying out a reaction selected from the following group to form a compound of formula II:
(b-1) in an inert solvent, reacting the intermediate of formula II with $R^1$—NH—$R^2$ to form a compound of formula I; or
(b-2) in an inert solvent, reacting the intermediate of formula II with potassium phthalimide to form an intermediate of formula III, and subjecting the intermediate of formula III to hydrazinolysis reaction to form a compound of formula I.

In the seventh aspect of the present invention, it provides an intermediate of formula II or III,

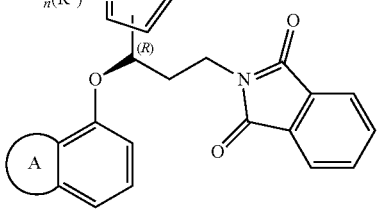

wherein X, A, $R^3$ and n are as defined in the fourth aspect of the present invention.

In the eighth aspect of the present invention, it provides a method for preparing the intermediate according to the seventh aspect of the present invention,

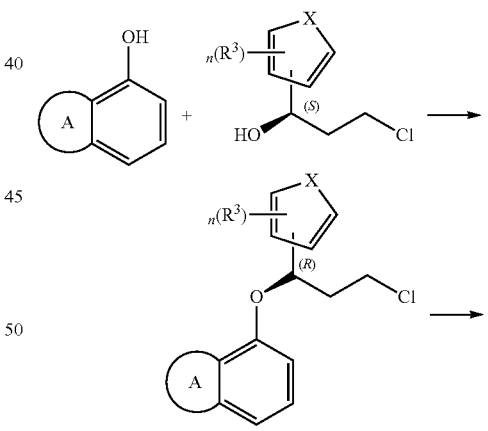

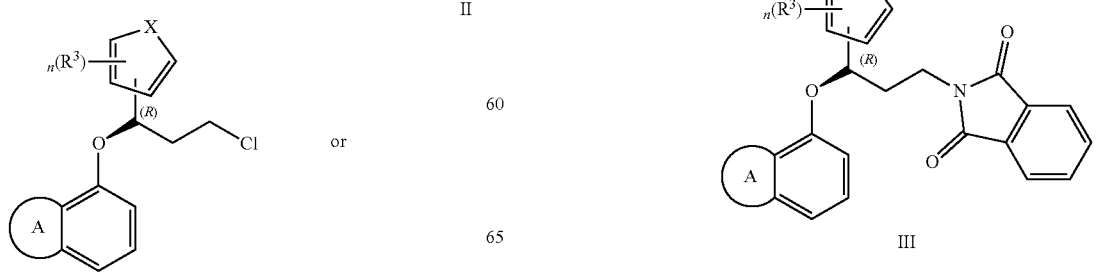

wherein X, A, R³ and n are as defined in the fourth aspect of the present invention;
(1) the method comprises:
(i) in an inert solvent and in presence of a condensing agent, reacting a compound of

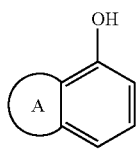

with (S)-1-((R³)ₙ-five-membered heteroaryl)-3-chloro-propanol, thereby forming an intermediate of formula II;

or (2) the method comprises:
(i) in an inert solvent and in presence of a condensing agent, reacting a compound of

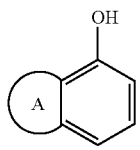

(S)-1-((R³)ₙ-five-membered heteroaryl)-3-chloro-propanol, thereby forming an intermediate of formula II;
(ii) in an inert solvent, reacting the intermediate of formula II with potassium phthalimide, thereby forming an intermediate of formula III.

In another preferred embodiment, the intermediate is selected from the following group:

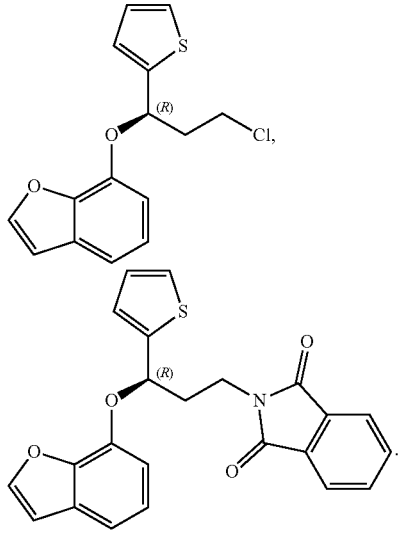

In the ninth aspect of the present invention, it provides a method for non-therapeutically and non-diagnostically inhibiting activity of transient receptor potential channel protein in vitro, which comprises contacting a transient receptor potential channel protein or a cell expressing the protein with the compound, or a pharmaceutically acceptable salt, or a prodrug thereof according to the third and/or fourth aspect of the present invention, thereby inhibiting activity of transient receptor potential channel protein.

In the tenth aspect of the present invention, it provides a method for inhibiting transient receptor potential channel protein or preventing and/or treating a disease related to transient receptor potential channel protein (TRP), which comprises administering the compound, or a pharmaceutically acceptable salt, or a prodrug thereof according to the third and/or fourth aspect of the present invention to a subject in need of.

In another preferred embodiment, the subject comprises human and non-human mammals (rodent, rabbit, monkey, domestic animal, dog, cat, etc.).

In the eleventh aspect of the present invention, it provides a compound, or a pharmaceutically acceptable salt, or a prodrug thereof;
wherein the compound has a structure of formula G:

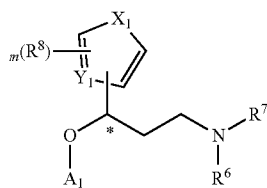

wherein
$A_1$ is

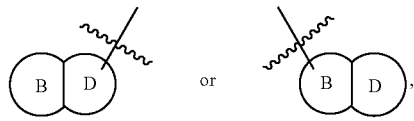

wherein ring B is a substituted or unsubstituted 5-7 membered carbocyclic ring, a substituted or unsubstituted 5-7 membered heterocyclic ring, substituted or unsubstituted 5-7 membered heteroaryl, or substituted or unsubstituted $C_6$-$C_{12}$ aryl; ring D is substituted or unsubstituted 5-7 membered heteroaryl, or substituted or unsubstituted $C_6$-$C_{12}$ aryl; and when $A_1$ is substituted or unsubstituted aromatic structure, $A_1$ contains 1-3 heteroatoms selected from the group consisting of N, O and S;

wherein the heterocyclic ring or heteroaryl contains 1-3 heteroatoms selected from the group consisting of N, O and S;

$R^6$ and $R^7$ are each independently hydrogen, substituted or unsubstituted $C_1$-$C_6$ alkyl, substituted or unsubstituted $C_3$-$C_7$ cycloalkyl, substituted or unsubstituted $C_2$-$C_4$ acyl, or substituted or unsubstituted $C_2$-$C_6$ ester group, or $R^6$ and $R^7$ and their linking N atom constitute substituted or unsubstituted $C_3$-$C_7$ heterocycloalkyl; wherein the heterocycloalkyl contains 1-2 N atoms and 0-1 O or S atom;

$X_1$ is carbon atom, oxygen atom, sulfur atom or nitrogen atom;

$Y_1$ is carbon atom or nitrogen atom;

at least one of $X_1$ and $Y_1$ is heteroatom;

$R^8$ is hydrogen, halogen, substituted or unsubstituted $C_1$-$C_6$ alkyl, or substituted or unsubstituted $C_3$-$C_7$ cycloalkyl;

m is 1, 2, 3, 4 or 5;

"*" represents a chiral carbon atom, and the absolute configuration of the chiral carbon atom is R type and S type;

wherein, the term "substituted" means that one or more (preferably 1, 2, 3) hydrogen atoms on the group are substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 5- or 6-membered aryl or heteroaryl (preferably $C_6$ aryl or $C_5$ heteroaryl).

In the invention, it should be understood that in the compound having formula G structure, "*" represents a chiral carbon atom, and the absolute configuration of the chiral carbon atom is R-type and S-type, which means racemic type.

In another preferred embodiment, $A_1$ is

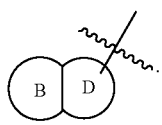

In another preferred embodiment, $A_1$ is not naphthalene ring.

In another preferred embodiment, $A_1$ is substituted or unsubstituted $C_6$-$C_{12}$ bicyclic heteroaryl, substituted or unsubstituted 5-6 membered heterocycle-bis-phenyl, substituted or unsubstituted 5-6 membered heterocycle-bis-5-6 membered heteroaryl, or substituted or unsubstituted $C_6$-$C_{12}$ benzoalicyclic group.

In another preferred embodiment, the $C_6$-$C_{12}$ bicyclic heteroaryl is quinolinyl, isoquinolinyl, phthalimidyl, benzofuranyl, benzothienyl, indolyl, benzooxazolyl, benzothiazolyl, quinoxalinyl, imidazopyridyl or benzimidazolonyl.

In another preferred embodiment, the $C_6$-$C_{12}$ benzoalicyclic group comprises indanyl, tetrahydronaphthyl or dihydronaphthyl.

In another preferred embodiment, $A_1$ is substituted or unsubstituted benzofuranyl, benzothienyl, or indanyl.

In another preferred embodiment, at least one of $X_1$ and $Y_1$ is heteroatom.

In another preferred embodiment, $X_1$ is S or O.

In another preferred embodiment, $X_1$ is S.

In another preferred embodiment, the heteroaryl contains 1-3 heteroatoms selected from the group consisting of N, O and S.

In another preferred embodiment, the term "substituted" means that 1-4 (preferably 1, 2, or 3) hydrogen atoms on the group are substituted by a substituent selected from the group consisting of $C_1$-$C_3$ alkyl, $C_3$-$C_7$ cycloalkyl, $C_1$-$C_3$ haloalkyl, halogen, nitro, cyano, hydroxyl, carboxyl, $C_2$-$C_4$ ester group, $C_2$-$C_4$ amide group, $C_1$-$C_4$ alkoxy, $C_1$-$C_6$ haloalkoxy, benzyl, 5- or 6-membered aryl or heteroaryl (preferably $C_6$ aryl or $C_5$ heteroaryl).

In another preferred embodiment, $A_1$ is substituted or unsubstituted $C_6$-$C_{12}$ bicyclic heteroaryl, substituted or unsubstituted 5-6 membered heterocycle-bis-phenyl, substituted or unsubstituted 5-6 membered heterocycle group-bis-5-6 membered heteroaryl, or substituted or unsubstituted $C_6$-$C_{12}$ benzoalicyclic group.

In another preferred embodiment, $R^6$ and $R^7$ are each independently hydrogen atom, $C_1$-$C_3$ alkyl, or $C_2$-$C_4$ acyl; or $R^6$ and $R^7$ and their linking N atom constitute tetrahydropyrrolyl substituted by carboxyl or $C_2$-$C_4$ ester group.

In another preferred embodiment, $R^8$ is hydrogen atom, halogen, or substituted or unsubstituted $C_1$-$C_3$ alkyl.

In another preferred embodiment, $A_1$ is quinolinyl, isoquinolinyl, phthalimidyl, benzofuranyl, benzothienyl, indolyl, benzoxazolyl, benzothiazolyl, quinoxalinyl, imidazopyridyl, benzimidazolonyl, indanyl, tetrahydronaphthyl or dihydronaphthyl.

In another preferred embodiment, $R^6$ and $R^7$ are each independently hydrogen, methyl, or acetyl, or $R^1$, $R^2$ and their linking N atom constitute proline group or proline methyl ester group.

In another preferred embodiment, $R^8$ is hydrogen atom, chlorine atom or methyl.

In another preferred embodiment, the compound of formula G is selected from the following group:

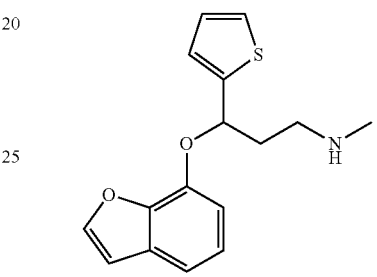

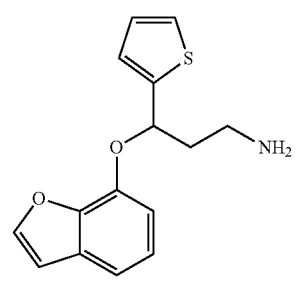

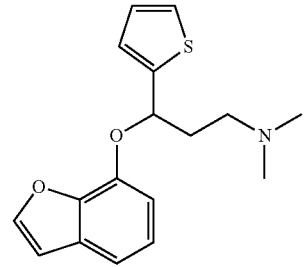

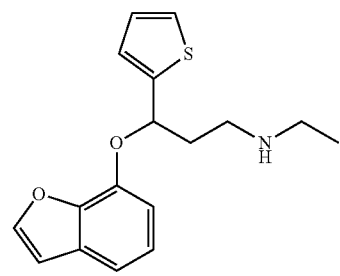

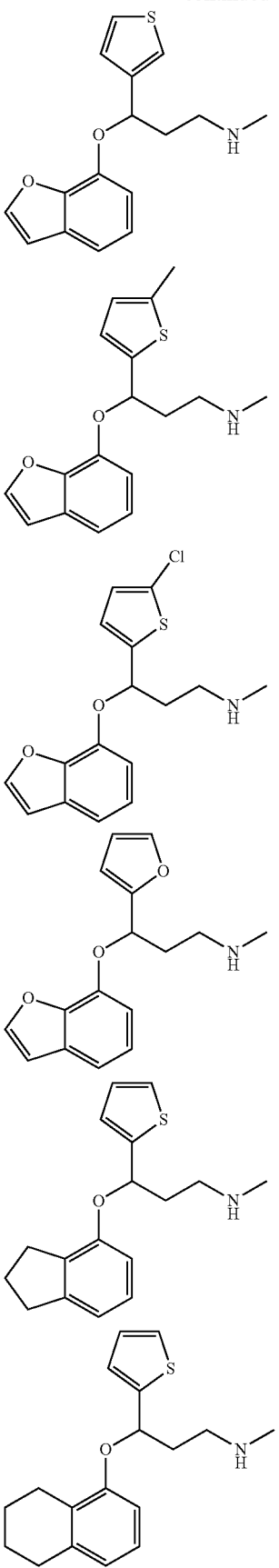

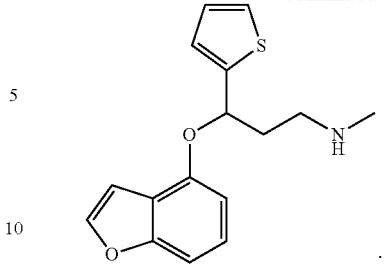

In the twelfth aspect of the present invention, it provides a use of a compound of formula G according to the eleventh aspect of the present invention for (a) preparing a transient receptor potential channel protein (TRP) inhibitor; or (b) preparing a medicine for preventing and/or treating a disease related to transient receptor potential channel protein (TRP).

In another preferred embodiment, the transient receptor potential channel protein (TRP) is TRPA1.

In another preferred embodiment, the disease related to transient receptor potential channel protein (TRP) is selected from the group consisting of pain, epilepsy, inflammation, respiratory disorder, pruritus, urinary tract disorder and inflammatory bowel disease.

In another preferred embodiment, the pain comprises acute inflammatory pain, chronic inflammatory pain, visceral pain, neurogenic pain, fibromyalgia, headache, neuralgia or cancer-induced pain.

In another preferred embodiment, the disease related to transient receptor potential channel protein (TRP) is selected from the group consisting of pain, epilepsy, inflammation, respiratory disorder, pruritus, urinary tract disorder, inflammatory bowel disease, and a combination thereof.

In another preferred embodiment, the pain is selected from the group consisting of acute pain, inflammatory pain, visceral pain, neurogenic pain, fibromyalgia, headache, neuralgia, mixed pain, pain caused by cancer, and a combination thereof.

In another preferred example, the acute pain is injury pain or postoperative pain.

In another preferred example, the inflammatory pain is chronic inflammatory pain.

In another preferred example, the inflammatory pain is osteoarthritis pain or rheumatoid arthritis pain.

In another preferred example, the headache is migraine or muscle tension pain.

In another preferred example, the neuralgia is trigeminal neuralgia, diabetic pain, sciatica or post-zoster neuralgia.

In the thirteenth aspect of the present invention, it provides a method for preparing the compound of formula G, or a pharmaceutically acceptable salt, or a prodrug thereof according to the eleventh aspect of the present invention, wherein the method comprises: in an inert solvent, reacting an intermediate of formula G-1 with $R^6$—NH—$R^7$, thereby forming the compound:

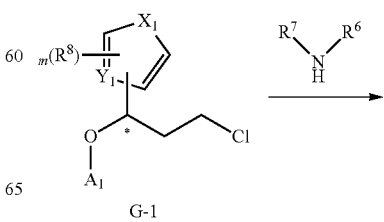

G-1

-continued

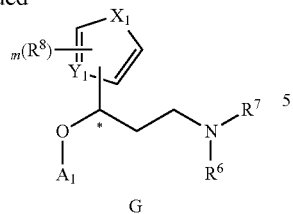

wherein, $X_1$, $Y_1$, $A_1$, $R^6$, $R^7$, $R^8$ and "*" are as defined in the eleventh aspect of the present invention.

In the fourteenth aspect of the present invention, it provides a method for non-therapeutically and non-diagnostically inhibiting activity of transient receptor potential channel protein in vitro, which comprises contacting a transient receptor potential channel protein or a cell expressing the protein with the compound of formula G, or a pharmaceutically acceptable salt, or a prodrug thereof according to the eleventh aspect of the present invention, thereby inhibiting activity of the transient receptor potential channel protein.

In the fifteenth aspect of the present invention, it provides a method for inhibiting transient receptor potential channel protein or preventing and/or treating a disease related to transient receptor potential channel protein (TRP), which comprises administering a compound of formula G, or a pharmaceutically acceptable salt, or a prodrug thereof according to the eleventh aspect of the present invention to a subject in need of.

It should be understood that, in the present invention, each of the technical features specifically described above and below (such as those in the Examples) can be combined with each other, thereby constituting new or preferred technical solutions which need not be redundantly described one-by-one.

EMBODIMENTS FOR CARRYING OUT THE INVENTION

Figure 1:
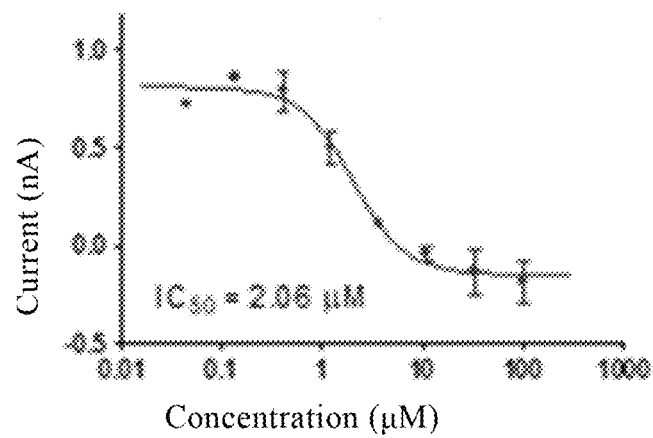
FIG. 1 shows the TRPA1 inhibitory activity ($IC_{50}$) of compound I-1 in the automated patch clamp test.

Based on an extensive and intensive research, the inventors have unexpectedly and firstly developed a compound, or a pharmaceutically acceptable salt, or a prodrug thereof, wherein the compound has a structure of formula I, Z or G. The experimental results of the present invention have shown that the compound of the present invention have significant inhibitory effect on TRP channel. The compound of the present invention can effectively treat a pain related to TRP (especially TRPA1) targets. On this basis, the inventors has completed the present invention.

Terms

As used herein, the terms "comprise", "comprising", and "containing" are used interchangeably, which not only comprise closed definitions, but also semi-closed and open definitions. In other words, the term comprises "consisting of" and "essentially consisting of".

As used herein, "$R^1$", "R1" and "$R_1$" have the same meaning and can be used interchangeably. The other similar definitions have the same meaning.

As used herein, the terms "$C_1$-$C_6$ alkyl", "$C_1$-$C_3$ alkyl" or "$C_1$-$C_4$ alkyl" refer to a linear or branched chain alkyl with 1-6, 1-3 or 1-4 carbon atoms, such as methyl, ethyl, propyl, isopropyl, butyl, isobutyl, sec-butyl, tert-butyl, or the like.

As used herein, the term "$C_1$-$C_6$ alkoxy" refers to a linear or branched alkoxy having 1 to 6 carbon atoms, such as methoxyl, ethoxyl, propoxyl, isopropoxyl, butoxyl, isobutoxyl, sec-butoxyl, tert-butoxyl, pentoxyl, hexyloxyl, or the like.

As used herein, the term "$C_6$-$C_{12}$ benzoalicyclic group" refers to a group having 6-12 carbon atoms, comprising indanyl, tetrahydronaphthyl, dihydronaphthyl, or the like.

As used herein, the term "$C_1$-$C_6$ haloalkoxy" means that one or more hydrogen atoms of a linear or branched alkoxy having 1 to 6 carbon atoms are substituted by halogen, such as monochloromethoxy, monochloroethoxy, or the like.

As used herein, the term "$C_3$-$C_7$ cycloalkyl" refers to a cycloalkyl with 3-7 carbon atoms, which comprises monocyclic, bicyclic or polycyclic ring, such as cyclopropyl, cyclobutyl, methylcyclobutyl, cyclopentyl, cycloheptyl, or the like.

As used herein, the term "$C_2$-$C_4$ ester group" refers to a group having $C_1$-$C_3$ alkyl-COO— structure or a group having —COO—$C_1$-$C_5$ alkyl structure, wherein the alkyl can be linear or branched, such as $CH_3COO$—, $C_2H_5COO$—, $C_3H_8COO$—, $(CH_3)_2CHCOO$—, —$COOCH_3$, —$COOC_2H_5$, —$COOC_3H_8$, or the like.

As used herein, the term "$C_2$-$C_4$ amide group" refers to a group having $C_1$-$C_3$ alkyl-CO—NH— structure or a group having —NH—CO—$C_1$-$C_3$ alkyl structure, wherein the alkyl can be linear or branched, such as $CH_3$—CO—NH—, $C_2H_5$—CO—NH—, $C_3H_8$—CO—NH—, —$COOCH_3$, —CO—NH—$C_2H_5$, —CO—NH—$C_3H_8$, or the like.

As used herein, the term "$C_2$-$C_4$ acyl" refers to a group having $C_1$-$C_3$ alkyl-CO— structure, wherein the alkyl can be linear or branched, such as $CH_3$—CO—, $C_2H_5$—CO—, $C_3H_8$—CO—, or the like.

As used herein, the term "$C_3$-$C_7$ heterocycloalkyl" refers to monocyclic and polycyclic heterocycles (preferably monocyclic heterocycle) having 3-7 ring carbon atoms and 1-3 heteroatoms (preferably containing one nitrogen atom which is the nitrogen atom commonly adjacent to $R^1$ and $R^2$), such as piperidinyl, tetrahydropyrrolyl, or the like.

As used herein, the term "5-7 membered carbocyclic ring" refers to any stable 5-, 6- or 7-membered monocyclic, bicyclic or polycyclic ring. The carbocyclic ring can be saturated, partially unsaturated, or unsaturated, but cannot be aromatic ring. Examples of carbocyclic ring comprise, but are not limited to, cyclopropyl, cyclobutyl, cyclobutenyl, cyclopentyl, cyclopentenyl, cyclohexyl, cyclohexenyl, cycloheptyl, cycloheptenyl, or the like.

As used herein, the term "5-7 membered heterocyclic ring" refers to any stable monocyclic, bicyclic or polycyclic ring. The heterocyclic ring contains one or more (preferably 1, 2 or 3) heteroatoms selected from N, O and S, and the number of ring atoms in the heterocyclic ring is 5-7. The heterocyclic ring can be saturated, partially unsaturated, unsaturated ring, but is not aromatic ring. It should be understood that when there are multiple heteroatoms, the heteroatoms can be same, partially same, or completely different.

As used herein, the terms "$C_1$-$C_3$ haloalkyl" mean that one or more hydrogen atoms of a linear or branched alkyl having 1-3 carbon atoms are substituted by halogen, such as monochloromethanyl, dichloroethanyl, trichloropropanyl, or the like.

As used herein, the term "$C_1$-$C_4$ carboxyl" refers to $C_1$-$C_3$ alkyl-COOH, wherein the alkyl can be linear or branched, such as $CH_3COOH$, $C_2H_5COOH$, $C_3H_8COOH$, $(CH_3)_2CHCOOH$, or the like.

As used herein, the term "$C_6$-$C_{12}$ aryl" refers to a monocyclic or bicyclic aromatic hydrocarbon group having 6 to 12 carbon atoms in the ring, such as phenyl, naphthyl, biphenyl, or the like.

As used herein, the term "5-7 membered heteroaryl ring" refers to an aromatic heterocyclic ring having one to more (preferably 1, 2, or 3) heteroatoms selected from N, O and S, and having 5-7 ring atoms. It should be understood that when there are multiple heteroatoms, the heteroatoms can be same, partially same, or completely different. For example, examples of 5-membered heteroaromatic ring comprise but are not limited to pyrrole ring, furan ring, thiophene ring, imidazole ring, oxazole ring, thiazole ring, examples of 6-membered heteroaromatic ring comprise but are not limited to pyridine ring, pyrazine ring, pyridazine ring, pyrimidine ring, or the like.

As used herein, the term "5- or 6-membered heteroaryl" refers to an aromatic group having one to more (preferably 1, 2, or 3) heteroatoms selected from N, O, and S, and having 5 or 6 ring atoms. It should be understood that when there are multiple heteroatoms, the heteroatoms can be same, partially same, or completely different. For example, examples of 5-membered heteroaryl comprise but are not limited to pyrrolyl, furyl, thienyl, imidazolyl, oxazolyl, thiazolyl, or the like.

As used herein, the term "6-membered heteroaryl" refers to an aromatic group having 6 ring atoms, and the ring atoms are all carbon atoms, such as phenyl, or the like.

As used herein, the term "halogen" refers to F, Cl, Br, and I.

As used herein,

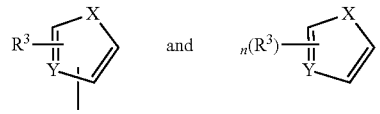

have the same meaning, and both represent unsubstituted heteroaryl or heteroaryl substituted by 1 to 5 (preferably 1 to 3) $R^3$.

As used herein, the term "substituted" means that a hydrogen atom on the group is replaced by non-hydrogen atom group, but the valence requirement must be met and the substituted compound is chemically stable. In the specification, it should be understood that each substituent is unsubstituted, unless it is expressly described as "substituted" herein. In a preferred embodiment, any of the term "substituted" means that 1-4 (preferably 1, 2, 3, or 4) hydrogen atoms on the group are each independently substituted by a substituent selected from the group consisting of $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester group, $C_2$-$C_4$ amide group, $C_1$-$C_6$ alkoxyl, $C_1$-$C_6$ haloalkoxy, benzyl, 6-membered aryl or 5- or 6-membered heteroaryl (preferably $C_5$ heteroaryl).

It should be understood that substituents can be connected to a parent group or substrate on any atom in present invention, unless the connection violates the valence requirement; and the same or different substituents can be on the same atom or different atoms.

Similarly, it should be understood that those skill in the art can select the substituents and substitution patterns on the compounds of the present invention to obtain chemically stable compounds, which can be obtained by techniques known in the art and synthesis method as described below. If it is substituted by more than one substituent group, it should be understood that the multiple groups can be on the same carbon or on different carbons, as long as a stable structure is produced.

In the present invention, the structure of R-duloxetine and S-duloxetine are as follows:

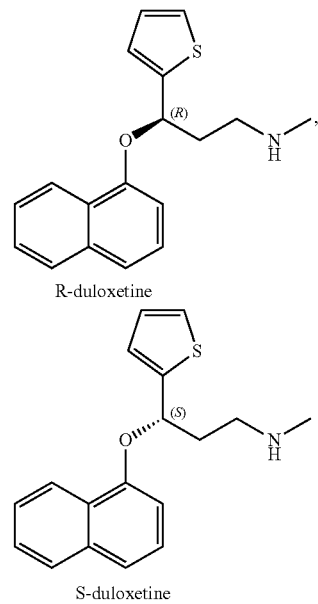

Active Ingredient

As used herein, the term "compound of formula I of present invention" refers to a compound of formula I, or a pharmaceutically acceptable salt, or a prodrug thereof. It should be understood that the term also comprises a mixture of the above components.

As used herein, the term "compound of formula Z of present invention" refers to a compound of formula Z, or a pharmaceutically acceptable salt, or a prodrug thereof. It should be understood that the term also comprises a mixture of the above components.

As used herein, the term "compound of formula G of present invention" refers to a compound of formula G, or a pharmaceutically acceptable salt, or a prodrug thereof. It should be understood that the term also comprises a mixture of the above components.

The compound of the present invention not only has inhibitory effect on TRPA1, but also has certain inhibitory effect on other members of TRP family.

The term "pharmaceutically acceptable salt" refers to a salt formed by a compound of the present invention and an acid or a base suitable for use as a medicine. Pharmaceutically acceptable salts include inorganic salts and organic salts. A preferred type of salt is the salt formed by the compound of the present invention and an acid. Acids suitable for salt formation include (but are not limited to): inorganic acid such as hydrochloric acid, hydrobromic acid, hydrofluoric acid, sulfuric acid, nitric acid, phosphoric acid and the like; organic acid such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like; and acidic amino acid such as aspartic acid and glutamic acid. A preferred type of salt is a metal salt formed by the compound of the present invention and a base. Suitable bases for salt formation include (but are not limited to): inorganic base such as sodium hydroxide, potassium hydroxide, sodium carbonate, sodium bicarbonate, sodium phosphate and the like; and organic base such as ammonia, triethylamine, diethylamine and the like.

The preferred compounds of the present invention comprises any compound selected from Table 1:

TABLE 1

| No. | Chemical name | Structure |
|---|---|---|
| Compound I-1 | (R)-3-(benzofuran-7-yloxy)-N-methyl-3-(thiophen-2-yl)propyl-1-amine | 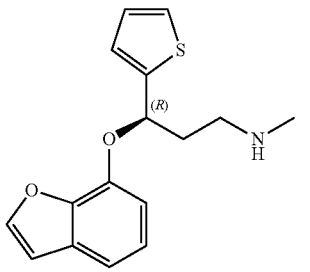 |
| Compound I-2 | (R)-3-(benzofuran-7-yloxy)-3-(thiophen-2-yl) propyl-1-amine | 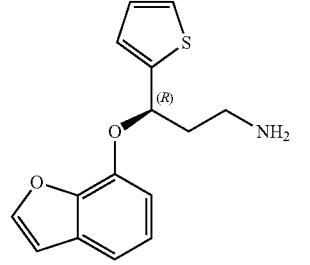 |
| Compound I-3 | (R)-3-(benzofuran-7-yloxy)-N,N-dimethyl-3-(thiophen-2-yl)propyl-1-amine | 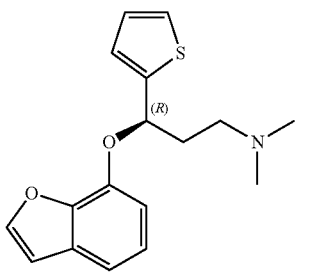 |

TABLE 1-continued

| No. | Chemical name | Structure |
|---|---|---|
| Compound I-4 | (R)-3-(benzofuran-7-yloxy)-N-ethyl-3-(thiophen-2-yl)propyl-1-amine | 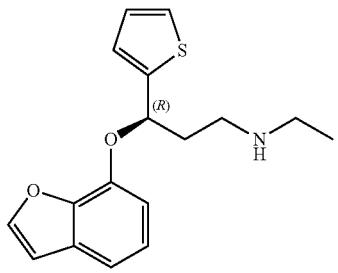 |
| Compound I-5 | (R)-3-(benzofuran-7-yloxy)-N-methyl-3-(thiophen-3-yl)propyl-1-amine | 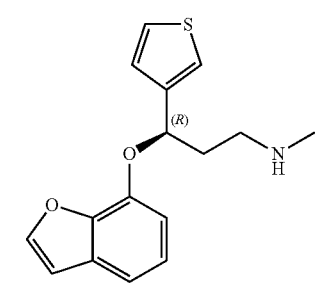 |
| Compound I-6 | (R)-3-(benzofuran-7-yloxy)-N-methyl-3-(5-methylthiophen-2-yl)propyl-1-amine | 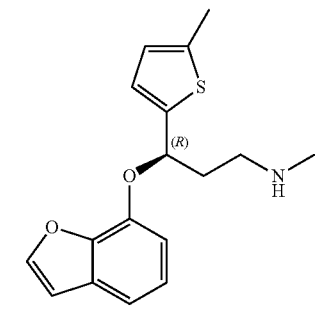 |
| Compound I-7 | (R)-3-(benzofuran-7-yloxy)-3-(5-chlorothiophen-2-yl)-N-methylpropyl-1-amine | 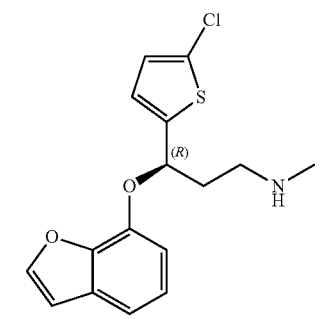 |
| Compound I-8 | (R)-3-(benzofuran-7-yloxy)-3-(furan-2-yl)-N-methylpropyl-1-amine | 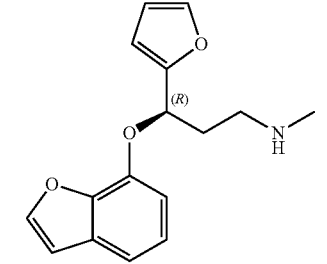 |

TABLE 1-continued

| No. | Chemical name | Structure |
|---|---|---|
| Compound I-9 | (R)-3-(2,3-dihydro-1H-inden-4-yl)oxy)-N-methyl-3-(thienyl-2-yl)propyl-1-amine | 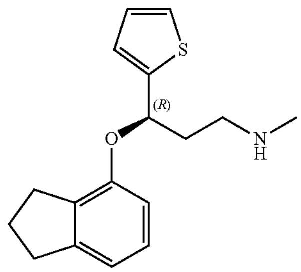 |
| Compound I-10 | (R)-N-methyl-3-((5,6,7,8-tetrahydronaphthalen-1-yl)oxy)-3-(thiophen-2-yl)propyl-1-amine | 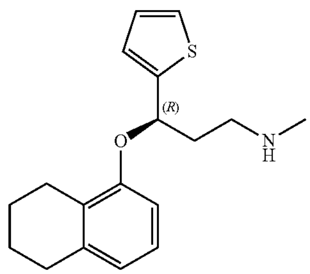 |
| Compound I-11 | (R)-3-(benzofuran-4-yloxy)-N-methyl-3-(thiophen-2-yl)propyl-1-amine | 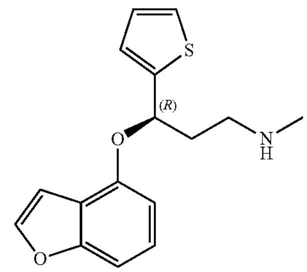 |

Preparation Method

The present invention further provides a method for preparing (R) 3-aryloxyl-3-five-membered heteroaryl propylamine compound of formula I.

The present invention further provides a method for preparing intermediates of formula II-III which are useful for preparing the above-mentioned compounds.

The specific synthesis methods are as follows:

Synthesis of Compounds of Formula I

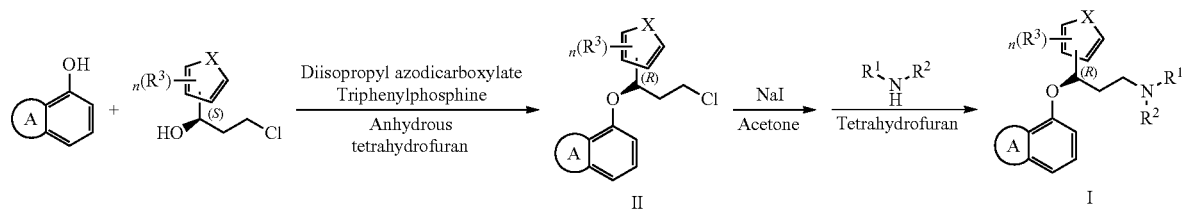

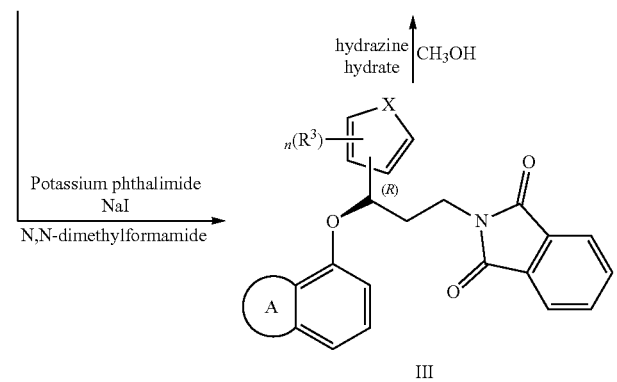

wherein A, X, R¹, R², R³ and n are as defined hereinabove;

1) The fused furan ring phenol or fused aliphatic ring phenol, (S)-1-((R³)$_n$-five-membered heteroaryl)-3-chloropropanol and triphenylphosphine are dissolved in anhydrous tetrahydrofuran (THF), diisopropyl azodicarboxylate is slowly added dropwise into the system in ice bath. After the dropwise addition is completed, the reaction is carried out at 20-25° C. overnight. After the reaction is completed, the system is directly spin-dried, and the residue is separated and purified by column chromatography to afford an intermediate of formula II.

2) The intermediate of formula II is dissolved in saturated sodium iodide acetone solution, the reaction is carried out at 50-70° C. overnight. After the reaction is completed, the solvent is spin-dried, and water is added into the system, the mixture is extracted three times with ethyl acetate, washed with saturated brine, dried with anhydrous sodium sulfate, filtered, and concentrated. The residue is dissolved in tetrahydrofuran solution, and amine solution or alcohol solution are added, the reaction is carried out at 20-25° C. overnight. After the reaction is completed, the solvent is spin-dried, sodium hydroxide aqueous solution is added into the system, the mixture is extracted three times with ethyl acetate, washed with saturated brine, dried with anhydrous sodium sulfate, filtered, and concentrated. The residue is separated by column chromatography to afford compound of formula I.

3) The intermediate of formula II, potassium phthalimide and sodium iodide are dissolved in N,N-dimethylformamide solution, the mixture is reacted at 70-90° C. overnight. After the reaction is completed, water is added into the system, the mixture is extracted three times with ethyl acetate, washed with water and saturated brine, dried with anhydrous sodium sulfate, filtered, concentrated, and the residue is separated by column chromatography to afford an intermediate of formula III.

4) The intermediate of formula III is dissolved in methanol, hydrazine hydrate is added, and the mixture is reacted at 20-25° C. overnight. After the reaction is completed, the solvent is spin-dried, and the residue is separated by column chromatography to afford compound of formula I.

Synthesis of Compound Salt

The compound of formula I, Z or G in present invention can be converted into its pharmaceutically acceptable salt by conventional methods. For example, a solution of corresponding acid can be added into the solution of above compounds, and the solvent is removed under reduced pressure after the salt is formed, thereby forming the corresponding salt of compounds of the present invention.

A preferred preparation method of compound I-1 hydrochloride of the present invention is as follows:

Preparation of (R)-3-(benzofuran-7-yloxy)-N-methyl-3-(thiophen-2-yl)propyl-1-amine hydrochloride (Compound 1-1 hydrochloride)

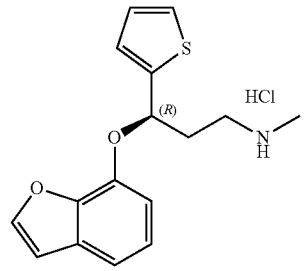

1 g of compound I-1 is dissolved in 10 ml of ethyl acetate solution, 0.3 ml of concentrated hydrochloric acid is added dropwise under ice bath condition, a white solid is precipitated out of the system, the reaction is continuously carried out under stirring for 5 min, then ice bath is removed. The reaction is carried out under stirring for 10 min. and the mixture is filtered with suction and washed 3 times with 5 ml of petroleum ether to afford 1.05 g of hydrochloride salt of compound I-1 as white solid (yield 93.18%, melting point: 136.2-136.9° C.).

Transient Receptor Potential Channel Protein (TRP)

Transient receptor potential channel protein is a protein superfamily composed of important cation channels on the cell membrane. Transient receptor potential channel protein comprises multiple subfamily, such as TRPA, TRPC, TRPM, TRPV, TRPML and TRPP subfamily.

TRPA1 is a member of TRPA subfamily, TRPA1 is also known as transient receptor potential ankyrin 1. Studies have found that TRPA1 channel protein is related to pain, epilepsy, inflammation, respiratory disorder, pruritus, urinary tract disorder, inflammatory bowel disease, etc. TRPA1 is a target used treat pain, epilepsy, inflammation, respiratory disorder, pruritus, urinary tract disorder and inflammatory bowel diseases, etc.

Uses

The present invention further provides a method for inhibiting transient receptor potential channel protein (TPR), and a method for treating a disease related to transient receptor potential channel protein.

The compound of formula I, Z or G of the present invention can inhibit transient receptor potential channel protein, thereby preventing or treating a disease related to transient receptor potential channel protein.

In the present invention, examples of the disease related to transient receptor potential channel protein comprise (but are not limited to): pain, epilepsy, inflammation, respiratory disorder, pruritus, urinary tract disorder, and inflammatory bowel disease, and a combinations therefore. Representatively, the pain comprises (but is not limited to): acute inflammatory pain, inflammatory pain (such as chronic inflammatory pain, osteoarthritis pain or rheumatoid arthritis pain), visceral pain, neurogenic pain, fibromyalgia, headache (such as migraine, muscle tension pain, etc.), neuralgia (such as trigeminal neuralgia, diabetic pain, post-zoster neuralgia, etc.), or pain caused by cancer.

In a preferred embodiment, the present invention provides a method for non-therapeutically and non-diagnostically inhibiting activity of transient receptor potential channel protein in vitro, which comprises in an in vitro culture system, contacting a transient receptor potential channel protein or a cell expressing the protein with the compound of formula I, Z or G, or a pharmaceutically acceptable salt, or a prodrug thereof in the present invention, thereby inhibiting activity of transient receptor potential channel protein.

In the present invention, the method for non-therapeutically and non-diagnostically inhibiting activity of transient receptor potential channel protein in vitro can be used for drug screening, quality control and other purposes. For example, In an in vitro culture system, contacting the transient receptor potential channel protein or cell expressing the protein with the compound of formula I, Z or G, or a pharmaceutically acceptable salt, or a prodrug thereof in present invention to screen compounds inhibiting activity of transient receptor potential channel protein as candidate drugs, and then animal experiments and clinical trials can be further used to study the therapeutic effect of candidate compounds on transient receptor potential channel protein and related diseases.

The present invention provides a method for inhibiting transient receptor potential channel protein, which is therapeutic or non-therapeutic. Generally, the method comprises administering the compound of formula I, Z or G, or a pharmaceutically acceptable salt, or a prodrug thereof in present invention to a subject in need of.

Preferably, the subject comprises human and non-human mammals (rodent, rabbit, monkey, livestock, dog, cat, and the like).

Pharmaceutical Composition and Administration Method

The invention provides a composition for inhibiting activity of transient receptor potential channel protein. The composition comprises (but is not limited to): pharmaceutical composition, food composition, dietary supplement, beverage composition, etc.

Typically, the composition is a pharmaceutical composition, which comprises the compound of formula I, Z or G, or a pharmaceutically acceptable salt thereof in present invention; and a pharmaceutically acceptable carrier.

In the present invention, the dosage form of pharmaceutical composition comprises (but are not limited to) oral preparation, injection and external preparation.

Representatively, the dosage form comprises (but is not limited to): tablet, capsule, injection, infusion, ointment, gel, solution, microsphere, and film.

The term "pharmaceutically acceptable carrier" refers to one or more compatible solid, semi-solid, liquid or gel filler, which are suitable for use in human or animals and must have sufficient purity and sufficient low toxicity. The "compatible" means each ingredient of the pharmaceutical composition and active ingredient of the drug can be blended with each other without significantly reducing the efficacy.

It should be understood that the carrier is not particularly limited. In the present invention, the carrier can be selected from materials commonly used in the art, or obtained by a conventional method, or is commercially available. Some examples of pharmaceutically acceptable carriers are cellulose and its derivatives (such as methylcellulose, ethylcellulose, hydroxypropylmethylcellulose, sodium carboxymethylcellulose, etc.), gelatin, talc, solid lubricants (such as stearic acid, magnesium stearate), calcium sulfate, plant oil (such as soybean oil, sesame oil, peanut oil, olive oil, etc.), polyols (such as propylene glycol, glycerin, mannitol, sorbitol, etc.), emulsifier (such as Tween), wetting agent (such as sodium lauryl sulfate), buffer agent, chelating agent, thickener, pH regulator, transdermal enhancer, colorant, flavoring agent, stabilizer, antioxidant, preservative, bacteriostatic agent, pyrogen-free water, etc.

Representatively, in addition to the active pharmaceutical ingredient, the liquid formulations can contain inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or a mixture thereof. In addition to these inert diluents, the composition can also contain adjuvants such as wetting agents, emulsifiers and suspensions and the like.

The pharmaceutical preparation should be matched with the mode of administration. The formulation of the present invention can also be used together with other synergistic therapeutic agents (including before, simultaneous or after administering). When a pharmaceutical composition or preparation is administered, a safe and effective dose of drug is administered to a subject in need (e.g. human or non-human mammals). The route of administration, patient health and other factors, should also be taken into account to determine the specific dose, which are within the ability of the skilled physicians.

The main advantages of the present invention include:

(a) The present invention provides novel compounds of formula I, Z or G which have excellent inhibitory activity on TRP channel (especially TRPA1).

(b) The compounds of the present invention have shown potent analgesic effects in several animal models.

(c) The compounds of the present invention have less toxicity and higher activity, so the safety window is larger.

(d) The compounds of the present invention have good druggability.

(e) The compounds of the present invention have excellent pharmacokinetic properties.

(f) The compounds of the present invention are suitable for oral administration.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1

(R)-7-(3-chloro-1-(thiophen-2-yl)propoxy)benzofuran (Intermediate II-1)

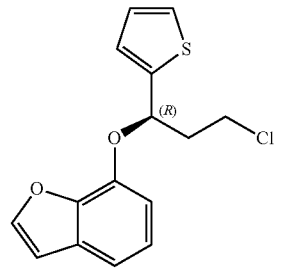

II-1

528 mg of (S)-3-chloro-1-(thiophen-2-yl)propan-1-ol, 400 mg of 7-hydroxybenzofuran and 862 mg of triphenylphosphine were dissolved in 30 ml of anhydrous tetrahydrofuran, 667 µl of diisopropyl azodicarboxylate was slowly added dropwise into the system under ice bath condition. After the dropwise addition was completed, the system was shifted to room temperature and reacted overnight. After the reaction was completed, the system was directly spin-dried, and the residue was separated and purified by column chromatography to afford 685 mg of Intermediate II-1 as colorless oil. Yield: 78.46%.

$^1$H NMR (500 MHz, CDCl$_3$) δ 7.62 (t, J=3.2 Hz, 1H), 7.41 (dd, J=1.8, 0.6 Hz, 1H), 7.24 (dt, J=8.1, 1.8 Hz, 1H), 7.15-7.11 (m, 1H), 6.91 (d, J=7.7 Hz, 1H), 6.77 (dd, J=8.0, 2.2 Hz, 1H), 6.35 (d, J=3.3 Hz, 1H), 6.33 (dd, J=3.3, 1.9 Hz, 1H), 5.75 (dd, J=8.4, 5.1 Hz, 1H), 3.93 (dd, J=11.1, 8.2, 5.4 Hz, 1H), 3.77-3.70 (m, 1H), 2.85-2.74 (m, 1H), 2.54-2.48 (m, 1H). MS (ESI, m/z): 292.93 (M+H)$^+$.

Example 2

(R)-3-(benzofuran-7-yloxy)-N-methyl-3-(thiophen-2-yl)propyl-1-amine (Compound I-1)

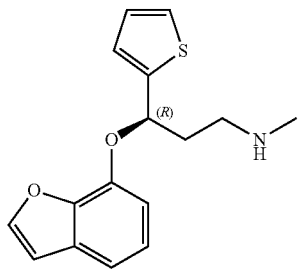

I-1

685 mg of intermediate II-1 was dissolved in saturated sodium iodide solution in acetone, and the mixture was refluxed overnight. After the reaction was completed, the solvent was spin-dried, water was added into the system, the mixture was extracted three times with ethyl acetate, washed with saturated brine, dried with anhydrous sodium sulfate, filtered, and concentrated. The residue was dissolved in 30 ml of tetrahydrofuran solution, 3 ml of 40% methylamine aqueous solution was added, the reaction was carried out overnight. After the reaction was completed, the solvent was spin-dried, sodium hydroxide aqueous solution was added into the system, then the mixture was extracted with ethyl acetate three times, washed with saturated brine, dried over anhydrous sodium sulfate, filtered, and concentrated. The residue was separated by column chromatography (methanol/dichloromethane=1:15) to afford 336 mg of compound I-1 as colorless oil. Yield: 49.97%.

$^1$H NMR (500 MHz, DMSO) δ 7.97 (d, J=2.1 Hz, 1H), 7.49 (dd, J=5.0, 1.1 Hz, 1H), 7.25-7.18 (m, 2H), 7.08 (t, J=7.9 Hz, 1H), 6.99 (dd, J=5.0, 3.5 Hz, 1H), 6.96 (d, J=7.9 Hz, 1H), 6.94 (d, J=2.1 Hz, 1H), 6.05 (dd, J=7.9, 5.2 Hz, 1H), 3.15-2.96 (m, 2H), 2.57 (s, 3H), 2.49-2.43 (m, 1H), 2.33-2.25 (m, 1H). MS (ESI, m/z): 288.0 (M+H)$^+$.

Example 3

(R)-2-(3-(benzofuran-7-yloxy)-3-(thiophen-2-yl)propyl)isoindoline-1,3-dione (Intermediate III)

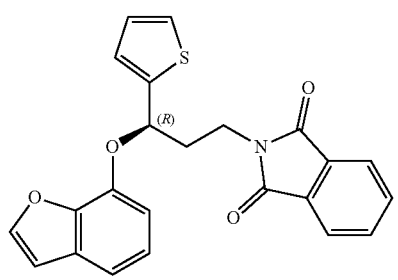

III 425 mg of intermediate II-1, 807 mg of potassium phthalimide and 100 mg of sodium iodide were dissolved in 15 ml of N,N-dimethylformamide, and the reaction was carried out at 90° C. under nitrogen protection overnight. After the reaction was completed, water was added into the system, the mixture was extracted three times with ethyl acetate, washed with water and saturated brine, dried over anhydrous sodium sulfate, filtered, and concentrated. The residue was separated by column chromatography (ethyl acetate/petroleum ether=1:5) to afford 412 mg of compound III as yellow solid. Yield: 70.35%.

$^1$H NMR (500 MHz, CDCl$_3$) δ 7.84-7.80 (m, 2H), 7.70 (dd. J=5.4, 3.1 Hz, 2H), 7.50 (d, J=2.0 Hz, 1H), 7.21 (dd, J=5.1, 1.4 Hz, 1H), 7.18 (dd, J=7.9, 0.9 Hz, 1H), 7.09 (d, J=3.1 Hz, 1H), 7.08-7.03 (m, 1H), 6.91 (dd, J=10.1, 5.1 Hz, 1H), 6.82 (d, J=7.3 Hz, 1H), 6.71 (d, J=2.2 Hz, 1H), 5.85 (dd, J=7.7, 5.4 Hz, 1H), 4.11-3.92 (m, 2H), 2.68 (dd, J=14.4, 7.3 Hz, 1H), 2.53-2.39 (m, 1H). MS (ESI, m/z): 403.99 (M+H)$^+$.

Example 4

(R)-3-(benzofuran-7-yloxy)-3-thiophen-2-yl)propyl-1-amine (compound I-2)

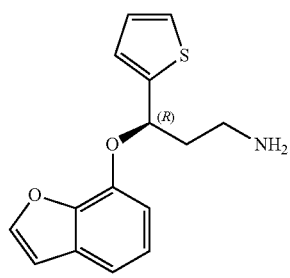

I-2

412 mg of Intermediate III and 270 mg of hydrazine hydrate were dissolved in 15 ml of methanol solution, and the reaction was carried out at room temperature overnight. After the reaction was completed, the solvent was spin-dried, and the residue was separated by column chromatography (methanol/dichloromethane=1:15) to afford 124 mg of compound I-2 as colorless oil. Yield: 44.42%.

¹H NMR (500 MHz, DMSO) δ 7.87 (d, J=2.3 Hz, 1H), 7.40 (dd, J=5.5, 1.6 Hz, 1H), 7.19-7.15 (m, 2H), 7.07 (t, J=7.9 Hz, 1H), 6.94 (dd, J=5.5, 3.8 Hz, 1H), 6.91 (d, J=7.7 Hz, 1H), 6.87 (d. J=2.4 Hz, 1H), 6.04 (m, 1H), 2.94-2.80 (m, 2H), 2.37-2.30 (m, 1H), 2.18 (dtd, J=11.8, 9.8, 5.1 Hz, 1H). MS (ESI, m/z): 273.98 (M+H)⁺.

Example 5

(R)-3-(benzofuran-7-yloxy)-N,N-dimethyl-3-(thiophen-2-yl)propyl-1-amine (compound I-3)

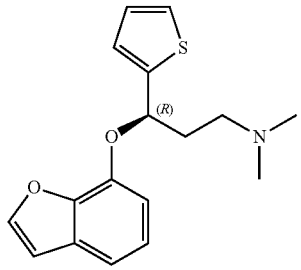

I-3

Except that methylamine aqueous solution was replaced with dimethylamine, the other required raw materials, reagents and preparation method were the same as the Example 2. 327 mg of compound I-3 as colorless oil was obtained. Yield: 44.76%.

1H NMR (500 MHz, CDCl3) δ 7.74 (d, J=2.5 Hz, 1H), 7.31 (dt, J=12.8, 6.4 Hz, 1H), 7.19 (dd, J=7.8, 0.9 Hz, 1H), 7.05-7.01 (m, 2H), 6.91 (dd, J=5.0, 3.5 Hz, 1H), 6.83 (dd, J=6.8, 6.1 Hz, 1H), 6.73 (d, J=4.2 Hz, 1H), 5.85-5.77 (m, 1H), 2.53-2.48 (m, 2H), 2.48-2.40 (m, 1H), 2.26 (s, 6H), 2.16 (dt, J=10.1, 4.9 Hz, 1H). MS (ESI, m/z): 302.01 (M+H)⁺.

Example 6

(R)-3-(benzofuran-7-yloxy)-N-ethyl-3-(thiophen-2-yl)propyl-1-amine (Compound I-4)

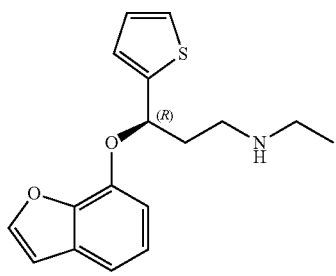

I-4

Except that methylamine aqueous solution was replaced with ethylamine, the other required raw materials, reagents and preparation method were the same as the Example 2. 478 mg of compound I-4 as colorless oil was obtained. Yield: 45.90%.

1H NMR (500 MHz, CDCl3) δ 7.67 (d. J=2.4 Hz, 1H), 7.25 (t, J=7.6 Hz, 2H), 7.15-6.89 (m, 2H), 6.85 (dd, J=5.5, 3.9 Hz, 1H), 6.74 (d, J=8.4 Hz, 1H), 6.66 (d, J=1.8 Hz, 1H), 5.81 (dd, J=9.2, 6.4 Hz, 1H), 3.25 (t, J=8.7 Hz, 2H), 3.15 (q, J=7.3 Hz, 2H), 2.78-2.66 (m, 1H), 2.60-2.49 (m, 1H), 1.51 (t, J=7.3 Hz, 3H). MS (ESI, m/z): 302.10 (M+H)⁺.

Example 7

(R)-3-(benzofuran-7-yloxy)-N-methyl-3-(thiophen-3-yl)propyl-1-amine (Compound I-5)

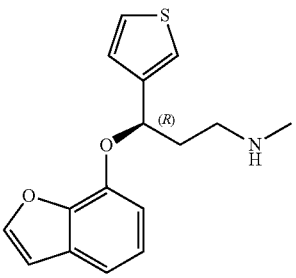

I-5

Except that (S)-3-chloro-1-(thiophen-2-yl)propyl-1-ol was replaced with (S)-3-chloro-1-(thiophen-3-yl)propyl-1-ol, the other required raw materials, reagents and preparation method were the same as the Examples 1-2. 313 mg of compound I-5 as colorless oil was obtained. Yield: 32.71%.

1H NMR (500 MHz, CDCl3) δ 7.63 (d, J=2.7 Hz, 1H), 7.31 (dd, J=5.5, 3.1 Hz, 1H), 7.27 (d. J=2.7 Hz, 1H), 7.20-7.14 (m, 2H), 7.07 (t, J=8.4 Hz, 1H), 6.76 (t, J=4.2 Hz, 1H), 6.73 (d, J=8.1 Hz, 1H), 5.66 (dd, J=7.7, 5.6 Hz, 1H), 2.95-2.83 (m, 2H), 2.50 (s, 3H), 2.44-2.33 (m, 1H), 2.26-2.14 (m, 1H). MS (ESI, m/z): 287.97 (M+H)⁺.

Example 8

(R)-3-(benzofuran-7-yloxy)-N-methyl-3-(5-methyl-thiophen-2-yl)propyl-1-amine (Compound I-6)

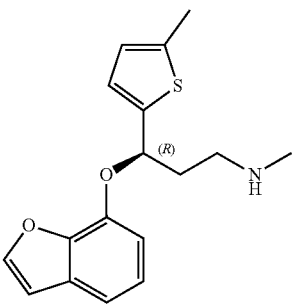

I-6

Except that (S)-3-chloro-1-(thiophen-2-yl)propyl-1-ol was replaced with (S)-3-chloro-1-(5-methylthiophen-2-yl)propyl-1-ol, the other required raw materials, reagents and preparation method were the same as Examples 1-2. 222 mg of compound I-6 as colorless oil was obtained. Yield: 26.42%.

1H NMR (500 MHz, CDCl3) δ 7.61 (d, J=2.0 Hz, 1H), 7.16 (dt, J=10.7, 5.4 Hz, 1H), 7.09 (d, J=7.9 Hz, 1H), 6.87 (d, J=7.7 Hz, 1H), 6.81 (d, J=4.4 Hz, 1H), 6.77 (dd, J=7.0, 2.2 Hz, 1H), 6.60-6.53 (m, 1H), 5.74 (dd, J=7.7, 5.6 Hz, 1H), 2.94-2.80 (m, 2H), 2.55 (s, 3H), 2.46-2.37 (m, 4H), 2.26-2.17 (m, 1H). MS (ESI, m/z): 302.01 (M+H)⁺.

Example 9

(R)-3-(benzofuran-7-yloxy)-3-(5-chlorothiophen-2-yl)-N-methylpropyl-1-amine (Compound I-7)

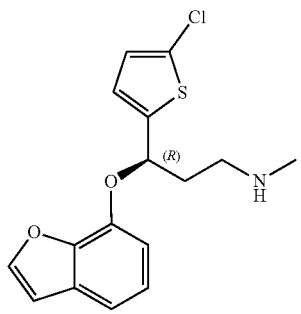

I-7

Except that (S)-3-chloro-1-(thiophen-2-yl)propyl-1-ol was replaced with (S)-3-chloro-1-(5-chlorothiophene-2-yl)propyl-1-ol, the other required raw materials, reagents and preparation method were the same as Examples 1-2. 275 mg of compound I-7 as colorless oil was obtained. Yield: 30.15%.

1H NMR (500 MHz, CDCl3) δ 7.63 (d, J=2.1 Hz, 1H), 7.22 (d, J=8.1 Hz, 1H), 7.11 (d, J=7.7 Hz, 1H), 6.91 (dd, J=13.4, 6.4 Hz, 2H), 6.82 (d, J=4.2 Hz, 1H), 6.76 (d. J=4.3 Hz, 1H), 5.70 (dd, J=8.7, 6.0 Hz, 1H), 3.11-3.02 (m, 2H), 2.53 (s, 3H), 2.48 (dt, J=21.6, 7.2 Hz, 1H), 2.27 (ddd, J=13.7, 12.0, 6.7 Hz, 1H). MS (ESI, m/z): 321.96 (M+H)⁺.

Example 10

(R)-3-(benzofuran-7-yloxy)-3-furan-2-yl)-N-methylpropyl-1-amine (Compound I-8)

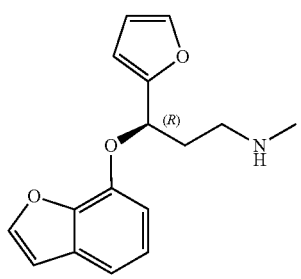

I-8

Except that (S)-3-chloro-1-(thiophen-2-yl)propyl-1-ol was replaced with (S)-3-chloro-1-(furan-2-yl)propyl-1-ol, the other required raw materials, reagents and preparation method were the same as Examples 1-2. 167 mg of the compound I-8 as colorless oil was obtained. Yield: 15.55%.

1H NMR (500 MHz, CDCl3) δ 7.56 (d, J=2.8 Hz, 1H), 7.33 (d, J=1.9 Hz, 1H), 7.17 (d, J=8.7 Hz, 1H), 7.01 (dd, J=11.5, 6.3 Hz, 1H), 6.74 (d, J=7.9 Hz, 1H), 6.67 (d, J=2.5 Hz, 1H), 6.26 (d, J=4.3 Hz, 1H), 6.15 (dd, J=4.2, 2.1 Hz, 1H), 5.56 (dd, J=8.4, 6.7 Hz, 1H), 3.11-2.96 (m, 2H), 2.64-2.55 (m, 4H), 2.40 (dd, J=12.4, 7.0 Hz, 1H). MS (ESI, m/z): 272.02 (M+H)⁺.

Example 11

(R)-3-((2,3-dihydro-1H-inden-4-yl)oxy)-N-methyl-3-(thienyl-2yl)propyl-1-amine (Compound I-9)

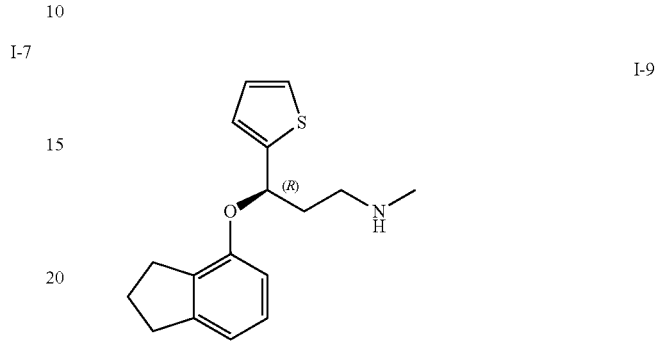

I-9

Except that 7-hydroxybenzofuran was replaced with 4-indanol, the other required raw materials, reagents and preparation method were the same as Examples 1-2. 116 mg of compound I-9 as colorless oil 1 was obtained. Yield: 20.75%.

1H NMR (500 MHz, CDCl3) δ 7.27 (dd. J=4.0, 2.1 Hz, 1H), 7.19-7.16 (m, 2H), 6.99 (t, J=8.4 Hz, 1H), 6.88 (d, J=7.7 Hz, 1H), 6.69 (d, J=8.5 Hz, 1H), 5.68 (dd, J=7.9, 4.8 Hz, 1H), 2.94 (dd, J=18.69, 9.1 Hz, 4H), 2.87 (ddd, J=10.0, 8.5 Hz, 4.0 Hz, 2H), 2.47 (s, 3H), 2.35-2.240 (m, 1H), 2.22-2.16 (m, 1H), 2.12-2.04 (m, 2H). MS (ESI, m/z): 288.03 (M+H)⁺.

Example 12

(R)—N-methyl-3-((5,6,7,8-tetrahydronaphthalen-1-yl)oxy)-3-(thiophen-2-yl)propyl-1-amine (Compound I-10)

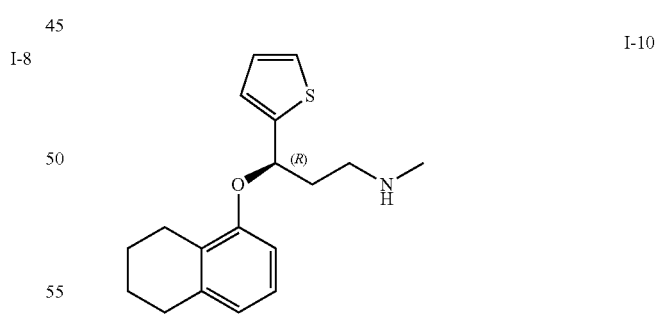

I-10

Except that 7-hydroxybenzofuran was replaced with tetrahydronaphthol, the other required raw materials, reagents and preparation method were the same as Examples 1-2. 103 mg of the compound I-10 as colorless oil was obtained. Yield: 25.17%.

1H NMR (500 MHz, CDCl3) δ 7.32 (d, J=2.2 Hz, 1H), 7.22-7.18 (m, 1H), 6.99-6.95 (m, 2H), 6.74 (d, J=8.5 Hz, 1H), 6.63 (d, J=8.8 Hz, 1H), 4.88 (dd, J=12.9, 4.4 Hz, 1H), 2.98-2.74 (m, 5H), 2.66-2.43 (m, 5H), 2.15-2.09 (m, 1H), 1.91-1.76 (m, 4H). MS (ESI, m/z): 302.0 (M+H)⁺.

Example 13

(R)-3-(benzofuran-4-yloxy)-N-methyl-3-(thiophen-2-yl)propyl-1-amine (compound I-11)

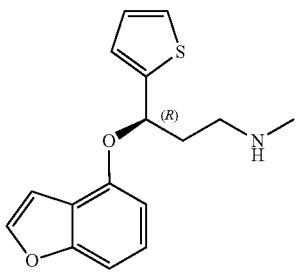

Except that 7-hydroxybenzofuran was replaced with 4-hydroxybenzofuran, the other required raw materials, reagents and preparation method were the same as Examples 1-2. 95 mg of compound I-11 as colorless oil was obtained. Yield: 14.06%.

1H NMR (500 MHz, CDCl3) δ 7.49 (d, J=2.8 Hz, 1H), 7.16 (d J=5.0, 1H), 7.11-7.04 (m, 3H), 6.89 (dd, J=5.2, 3.2 Hz, 2H), 6.74-6.65 (m, 1H), 5.81 (dd, J=7.5, 5.0 Hz, 1H), 3.16 (t, J=7.4 Hz, 2H), 2.76-2.67 (m, 1H), 2.65 (s, 3H), 2.62-2.51 (m, 1H). MS (ESI, m/z): 287.97 (M+H)$^+$.

Comparative Example 1

(S)-3-(benzofuran-7-yloxy)-N-methyl-3-(thiophen-2-yl)propyl-1-amine (Compound C1)

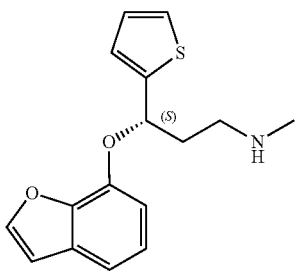

Except that (S)-3-chloro-1-(thiophen-2-yl)propan-1-ol was replaced with (R)-3-chloro-1-(thiophen-2-yl)propan-1-ol, the other required raw materials, reagents and preparation method were the same as Examples 1-2. 199 mg of compound C1 was obtained. Yield: 39.96%.

$^1$H NMR (400 MHz, CDCl$_3$) δ 7.63 (d, J=2.0 Hz, 1H), 7.20 (t, J=6.6 Hz, 2H), 7.08-6.99 (m, 2H), 6.88 (dd, J=4.9, 3.6 Hz, 1H), 6.80 (d, J=7.9 Hz, 1H), 6.75 (d, J=2.0 Hz, 1H), 5.93 (dd, J=8.2, 4.4 Hz, 1H), 3.30 (t, J=7.0 Hz, 2H), 2.82-2.69 (m, 4H), 2.65-2.54 (m, 1H). MS (ESI, m/z): 287.87 (M+H)$^+$.

Comparative Example 2

(R)-3-(benzofuran-7-yloxy)-N-methy-3-phenylpropyl-1-amine (compound C2)

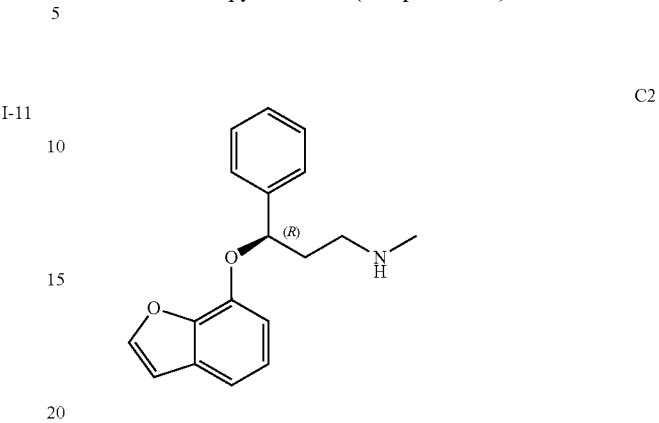

Except that (S)-3-chloro-1-(thiophen-2-yl)propan-1-ol was replaced with (S)-3-chloro-1-phenylpropane-1-ol, the other required raw materials, reagents and preparation method were the same as Examples 1-2. 147 mg of the compound C2 was obtained. Yield: 24.42%.

1H NMR (500 MHz, CDCl3) δ 7.64 (d, J=2.1 Hz, 1H), 7.45-7.40 (m, 2H), 7.32 (dd, J=10.3, 4.8 Hz, 2H), 7.24 (dt, J=2.4, 1.6 Hz, 1H), 7.12 (dd, J=7.8, 0.8 Hz, 1H), 6.96 (dd, J=10.4, 5.3 Hz, 1H), 6.74 (d, J=2.1 Hz, 1H), 6.63 (d, J=7.7 Hz, 1H), 5.49 (dd, J=8.3, 4.8 Hz, 1H), 2.90-2.80 (m, 2H), 2.46 (s, 3H), 2.39-2.29 (m, 1H), 2.16-2.06 (m, 1H). MS (ESI, m/z): 282.26 (M+H)$^+$.

Example 14

TRPA1 Inhibitory Activity

The inhibitory activity of some compounds in the examples of the present invention (as shown in Table 1) on transient receptor potential channel protein TRPA1 was tested in this example. The compound of formula A (WO2010075353) was used as a positive control compound:

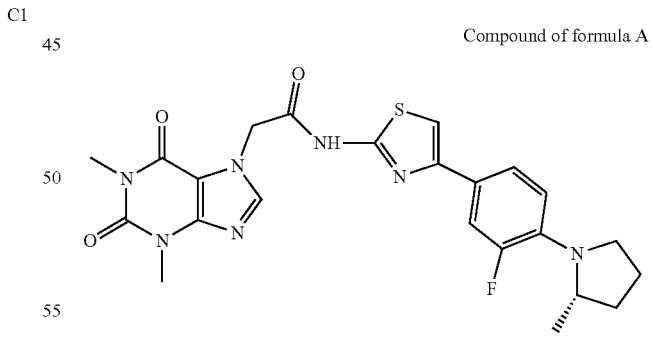

Compound of formula A

The method was as below:

IonWorks Barracuda (IWB) automated patch clamp detection was used as test method: HEK293 cells stably expressing TRPA1 were placed in DMEM medium containing 15 μg/mL Blasticidin S HCl, 200 μg/mL Hygromycin B and 10% FBS in the T175 culture flask, and cultured in 37° C., 5% CO$_2$ incubator. When the cell density reached about 80%, the culture medium was removed, rinsed with phosphate buffered saline (PBS) without calcium and magnesium, 3 mL of Trypsin was added to digest for 2 min, 7 mL of culture medium was added to terminate the digestion. The cells were collected to 15 mL centrifuge tube and centrifuged at 800 rpm for 3 min. After the supernatant was removed, the cells were added to appropriate volume of extracellular fluid for re-suspending, and the cell density was controlled at 2-3×10$^6$/mL for IWB experiment. Extracellular fluid formulation (in mM): 140 NaCl, 5 KCl, 1 MgCl$_2$, 10 HEPES, 0.5 EGTA, 10 Glucose (pH 7.4); intracellular fluid formulation (in mM): 140 CsCl, 10 HEPES, 5 EGTA, 0.1 CaCl$_2$, 1 MgCl$_2$ (pH 7.2). 28 mg/mL of amphotericin B was freshly prepared with DMSO on the day of experiment, and then final concentration of 0.1 mg/mL was prepared with intracellular fluid.

Population patch clamp (PPC) plate was used in IWB experiment. The entire detection process was automatically carried out by the instrument. Extracellular fluid was added into 384 wells of PPC plate, and 6 L of the intracellular fluid was added into plenum (under the PPC plate), 6 L of cell fluid was added for sealing test, and finally the intracellular fluid in plenum was replaced with amphotericin B-containing intracellular fluid to establish a whole-cell recording mode after perforating sealed cells. The sampling frequency for recording TPRA1 current was 10 kHz, the cells were clamped at 0 mV, the voltage stimulation command (channel protocol) was a ramp voltage from −100 mV to +100 mV for 300 ms. This voltage stimulation was applied every 10 s, mTRPA1 current was induced by 300 M AITC.

Data recording and current amplitude measurement export were carried out by IWB software (version 2.5.3, Molecular Devices Corporation, Union City, CA). No statistics was recorded for holes with sealing impedance lower than 20 M2. The original current data was corrected by software for leakage reduction. TRPA1 current amplitude was measured at +100 mV. Each PPC plate in the experiment had a dose-effect data of HC030031 as a positive control. If IC$_{50}$ value of HC030031 exceeded 3 times the average IC$_{50}$ value previously obtained on each plate, it would be re-tested. The dose-effect curve of compounds and IC$_{50}$ were fitted and calculated by GraphPad Prism 5.02 (GraphPad Software, San Diego, CA).

Experimental Results

Some compounds in the examples of the present invention were detected by IonWorks Barracuda (IWB) automated patch clamp detection method for IC$_{50}$ inhibitory activity. The activity data was shown in Table 2.

The results showed that the compounds of the present invention showed potent inhibitory activity on TRPA1, wherein the IC$_{50}$ values of 5 compounds on TRPA1 were 1-5 μM, the IC$_{50}$ values of 4 compounds on TRPA1 were 6-10 μM. FIG. 1 showed the inhibitory activity data IC$_{50}$ of compound I-1 of the present invention on TRPA1 was 2.06 μM. Therefore, it could be concluded that the compound of formula I-1 of the present invention had potent inhibitory activity on TRPA1.

In addition, the activity ratio of compound I-1 (containing heteroaryl) and comparative compound C2 (containing phenyl), i.e., IC$_{50}$ of compound C2/IC$_{50}$ of compound I-1 was about 6.3, which suggested that the compound of the present invention containing heteroaryl (such as compound I-1) had higher inhibitory activity on TRPA1.

Compared with a compound with benzene ring as A group, such as R-duloxetine, the IC$_{50}$ values of compound I-1, compound I-3, compound I-4, compound I-5, compound I-8 and compound I-9 were significantly decreased. The ratio of the IC$_{50}$ of R-duloxetine to the IC$_{50}$ of any of compound I-1, compound I-3, compound I-4, compound I-5, compound I-8 and compound I-9 was about 9.3 to 23.5. The results suggested that the compounds of the present invention with alicyclic ring or heteroaryl as A group had higher inhibitory activity on TRPA1.

Figure 2:
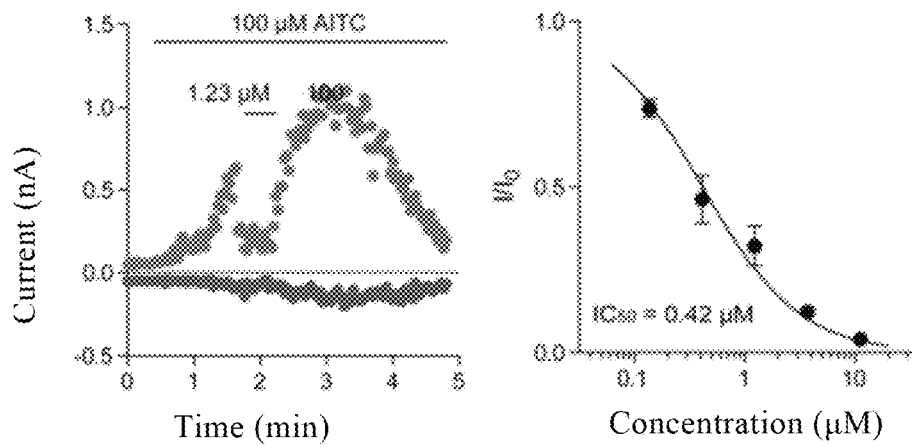
FIG. 2 shows the TRPA1 inhibitory activity ($IC_{50}$) of compound I-1 in the manual patch clamp test.

The TRPA1 inhibitory activity of compound I-1 was evaluated by manual patch clamp test method. As shown in FIG. 2, the test result was similar to that of the automatic patch clamp test method. In the manual patch clamp test method, the IC$_{50}$ of compound I-1 was 0.42 μM, showing potent inhibitory activity on TRPA1.

Example 15

Cytotoxicity Test

In this example, hepatotoxicity and neurotoxicity of compound I-1 and S-duloxetine were detected.

1. The Hepatotoxicity and Neurotoxicity of Compound I-1

HepG-2 and SH-SY5Y cells were placed in 10 cm dish and cultured at 37° C., 5% CO$_2$ in a cell incubator. Trypsin was used to digest and resuspend cells and cells were counted. The cells were transferred to 96-well plate with 8000 cells in a well (100 μl/well), cultured at 37° C., 5% CO$_2$ in a cell incubator for 24 hrs. A serial of gradient concentration dilutions of compound I-1 (prepared in example 2 of the present invention) with 2-fold dilution were prepared, and the system was 100 μL/well. The supernatant of cell culture system in the 96-well plate was

TABLE 2

Inhibitory activity data (IC$_{50}$, μM) of some compounds of the present invention on TRPA1 in the automated patch clamp detection test

| NO. | IC$_{50}$ (μM) | NO. | IC$_{50}$(μM) | NO. | IC$_{50}$(μM) |
|---|---|---|---|---|---|
| Compound I-1 | +++++ | Compound I-2 | ++++ | Compound I-3 | +++++ |
| Compound I-4 | +++++ | Compound I-5 | +++++ | Compound I-6 | ++++ |
| Compound I-8 | +++++ | Compound I-9 | ++++ | Compound I-11 | ++++ |
| Compound C2 (Comparative example 2) | +++ | Compound of formula A | + | R- duloxetine | ++ |

Activity: IC$_{50}$ (μM):
51-100: +
21-50: ++
11-20: +++
6-10: ++++
1-5: +++++ removed on the first day, and fresh-prepared drug concentration system was add into culture plate wells (duplicate wells were set). The cells were cultured at 37° C. 5% $CO_2$ in a cell incubator for 72 h. After the cell culture was completed, the supernatant of cell culture system was removed from 96-well plate, 100 μl of detection solution containing 10% CCK-8 medium was added into each well, and the cells were cultured at 37° C., 5% $CO_2$ in a cell incubator for 1 h. Microplate reader was used to measure the absorbance at 450 nm. Data was processed to calculate cytotoxicity, and $IC_{50}$ was calculated by GraphPad Prism. The cytotoxicity calculation formula was as follows: Cytotoxicity (%)=[A(0 Dosing)–A(Dosing)]/[A(0 Dosing)–A(control))×100

A (Dosing): the absorbance of wells containing cells, CCK-8 solution and drug solution.

A (control): the absorbance of wells containing medium and CCK-8 solution and without cells.

A (0 Dosing): the absorbance of wells containing cells and CCK-8 solution but without drug solution.

2. The Hepatotoxicity and Neurotoxicity of S-Duloxetine.

The test method was similar to the above-mentioned hepatotoxicity and neurocytotoxicity experiments of compound I-1 except that S-duloxetine was used instead of compound I-1.

Experimental Results

The results of hepatotoxicity (HepG2 cell) and neurotoxicity (SH-SY5Y) of compound I-1 were as follows:

The $IC_{50}$ of the hepatotoxicity and neurotoxicity of S-duloxetine was 33.33 μM and 28.59 μM, respectively, while the $IC_{50}$ of hepatotoxicity and neurotoxicity of compound I-1 of the present invention were about 113.80 μM and 100.70 μM, which suggested that the compounds of the present invention had significantly lower toxicity and side effects and had excellent safety.

Example 16

Evaluation of Therapeutic Effect of Compound I-1 on Acute Pain and Inflammatory Pain in Mice Formalin Pain Model.

Experimental Method

150 C57BL/6 mice (male, 9-week aged) were randomly divided into 15 groups, (each group had 10 mice) for the analgesic activity test of 3 compounds in the mice formalin pain model respectively: the compound I-1 group (compound I-1 prepared in Example 2 whose hydrochloride salt was used in the experiment), the S-duloxetine group (its hydrochloride salt was used in the experiment) and the compound C1 group (the compound C1 prepared in Comparative Example 1, whose hydrochloride salt was used in the experiment). Before the start of experiments, the mice were allowed to adapt to the experimental environment for 72 h with free feeding and drinking water. The test drugs were administered by intraperitoneal injection at a dosage as follows:

Compound I-1 group: blank vehicle (blank saline control), 0.1 mg/kg, 0.5 mg/kg, 1 mg/kg, 5 mg/kg and 10 mg/kg;

S-duloxetine group: blank vehicle (blank saline control), 1 mg/kg, 5 mg/kg, 10 mg/kg and 20 mg/kg;

Compound C1 group: blank vehicle (blank saline control), 0.1 mg/kg, 0.5 mg/kg, 1 mg/kg, 5 mg/kg and 10 mg/kg.

After administration, the mice were placed in a transparent, ventilated plexiglass cylinder for 1 h, and then 20 μl of 4% formalin solution was injected into the left hind plantar of mice of each group by microinjector, claw pain response in mice were real-time recorded by a mini-camera. The time length of licking left claw were used as an indicator of pain response, licking time in 0-10 min (phase I) and 10-60 min (phase II) were observed and recorded, and the statistical analysis was conducted. The half effective dose ($ED_{50}$) of 3 compounds were calculated: $ED_{50}$ referred to the dose of the drug which decreased licking time by half as compared with the blank control group. The smaller the $ED_{50}$ value was, the lower the effective analgesic dose of the compound was and the better the analgesic effect was.

Experimental Results

Figure 3:
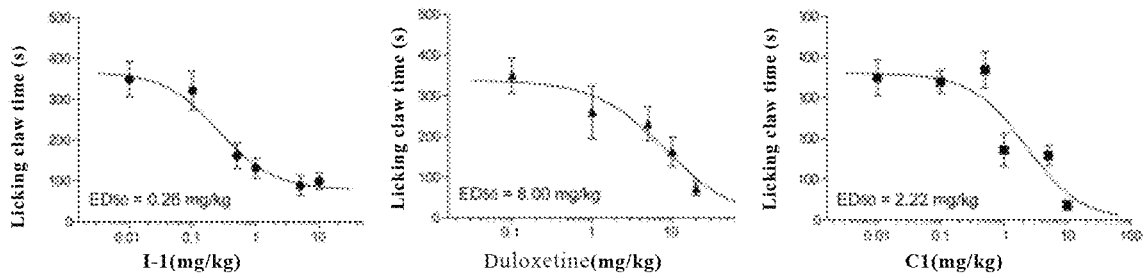
FIG. 3 shows $ED_{50}$ of compound I-1 of the present invention, S-duloxetine and comparative compound C1 in the mice formalin pain model.

The test results of the mice formalin pain model were shown in Table 3 and FIG. 3. Table 3 and FIG. 3 showed that all three compounds showed a dose-dependent analgesic activity. The licking time in phase II (10-60 min) of the compound I-1 of the present invention at a dosage of 0.5 mg/kg decreased by more than 50% as compared with the blank vehicle, and the analgesic effect $ED_{50}$ in phase II pain was 0.26 mg/kg. The $ED_{50}$ of S-duloxetine in phase II pain was 8.00 mg/kg, and the $ED_{50}$ of the comparative compound C1 in phase II pain was 2.22 mg/kg. From the above data, it could be seen that compound I-1 of the present invention showed extremely potent analgesic activity in the mice formalin pain model, and its $ED_{50}$ was 30.8 times stronger than S-duloxetine, and 8.5 times stronger than compound C1. The mice formalin model was a classical model for evaluating the drug effects on acute pain and inflammatory pain. Therefore, compound I-1 of the present invention had excellent therapeutic effect on acute pain and inflammatory pain.

TABLE 3

The statistical results of licking claw time of compound I-1 of the present invention, S-duloxetine and comparative compound C1 in phase II (10-60 min) at different dosages in the mice formalin model

| Dose | Licking claw time (s) | | |
|---|---|---|---|
| | Compound I-1 | S-duloxetine | Compound C1 |
| Blank Vehicle | 349.55 ± 43.09 | 349.55 ± 43.09 | 349.55 ± 43.09 |
| 0.1 mg/kg | 321.55 ± 47.75 | — | 339.35 ± 27.90 |
| 0.5 mg/kg | 161.25 ± 30.83 | — | 368.16 ± 44.46 |
| 1 mg/kg | 131.28 ± 23.99 | 259.97 ± 64.44 | 171.57 ± 39.69 |
| 5 mg/kg | 87.85 ± 25.15 | 230.49 ± 41.31 | 158.02 ± 25.18 |
| 10 mg/kg | 99.08 ± 19.73 | 162.83 ± 36.27 | 35.68 ± 11.77 |
| 20 mg/kg | — | 72.27 ± 17.29 | — |

Example 17

Evaluation of Therapeutic Effect of Compound I-1 on Acute Pain in Rat Hot Plate Pain Model.

Experimental Method

Sprague-Dawley male, mature and unmated rats were placed at hot and cold plate (product model: PE34, US IITC)

with constant 53±0.1° C. Mice with painful response such as licking claw, shaking claw or slightly jumping within 10-30 s were selected, and mice which evaded and jumped were abandoned. The 50 selected animals were weighed and randomly divided into 5 groups with 10 mice in each group: saline control group (vehicle, blank control), S-duloxetine group (its hydrochloride salt was used in experiment), gabapentin group, comparative compound C1 group (compound C1 prepared in Comparative Example 1, whose hydrochloride salt was used in the experiment) and compound I-1 group (compound I-1 prepared in Example 2, whose hydrochloride salt was used in the experiment). The test compound was freshly prepared on the day of administration. 0.9% NaCl physiological saline solution was prepared as solvent for later use. Appropriate amount of test compound was added into required volume of physiological saline and fully suspended, and the concentration of prepared drug was 1 mg/ml. The standard volume of administration to mice was 10 ml/kg, the administration mode was intraperitoneal administration, animals did not need to be fasted before administration. The dosage of S-duloxetine, compound C1 and compound I-1 was 30 mg/kg, and the dosage of gabapentin was 100 mg/kg. After administration, the latency of heat pain was measured at 0.5 h, 1 h and 2 h after administration. In order to prevent animals from being scalded on the hot plate, the maximum incubation time was set to 30 s. Maximum possible effect (MPE) % was used to evaluate analgesic effect of each compound, i.e., MPE %=[(Post drug latency-baseline latency)/(30−baseline latency)]×100. MPE % at different time points was recorded. The higher the value of MPE % was, the stronger the analgesic effect of the compound was.

Experimental Results

Figure 4:
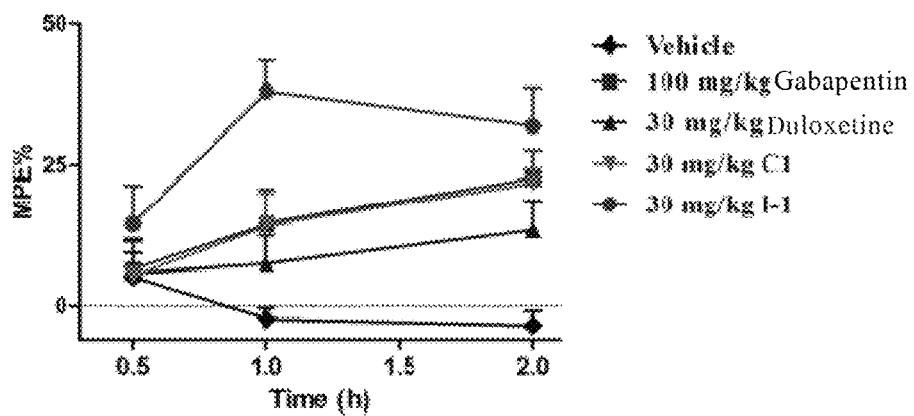
FIG. 4 shows a statistical graph of MPE % of compound I-1 of the present invention, S-duloxetine, comparative compound C1 and gabapentin at different times in the rat hot plate pain model.

The results of analgesic activity of compounds in the rat hot plate pain model were shown in Table 4 and FIG. 4. Table 4 and FIG. 4 showed that compared with the saline control group, compound I-1 of the present invention showed very potent analgesic effect at a dosage of 30 mg/kg with a significant difference. Compared with the positive control group, the analgesic activity of compound I-1 of the present invention was significantly stronger than 100 mg/kg of gabapentin within 2 h, and stronger than 10 mg/kg of duloxetine. The hot plate pain model was a classic model for evaluating the efficacy of drugs on acute pain. Therefore, the compounds of the present invention had excellent therapeutic effect on acute pain.

TABLE 4

MPE % statistical data of compound I-1, S-duloxetine, comparative compound C1 and gabapentin of the present invention in rat hot plate pain model at different times

| Compound | Dose | MPE % | | |
|---|---|---|---|---|
| | | 0.5 h | 1 h | 2 h |
| Saline control group | | 5.15 ± 4.31 | −2.31 ± 1.95 | −3.39 ± 2.47 |
| Compound I-1 | 30 mg/kg | 14.51 ± 6.87 | 38.03 ± 5.66 | 31.92 ± 6.79 |
| S-duloxetine | 30 mg/kg | 5.75 ± 5.74 | 7.44 ± 5.12 | 13.53 ± 4.99 |
| Compound C1 | 30 mg/kg | 5.29 ± 1.56 | 14.20 ± 5.71 | 21.83 ± 2.45 |
| Gabapentin | 100 mg/kg | 6.47 ± 5.49 | 14.56 ± 6.18 | 22.66 ± 4.93 |

Example 18

Evaluation of Therapeutic Effect of Compound I-1 on Visceral Pain and Inflammatory Pain in Mice Acetic Acid Writhing Pain Model Experimental Method Male ICR mice, 22-25 g, were fasted but allowed to drink water freely for 2 h before administration. All ICR mice were weighed and grouped randomly, each group had >10 animals. The negative control group was saline group (vehicle, blank control), and the positive control group was administrated with 10 mg/kg indomethacin (a non-steroidal anti-inflammatory drug), 10 mg/kg anisodamine (an antispasmodic drug with clinically analgesic activity), 10 mg/kg S-duloxetine (its hydrochloride salt was used in the experiment) and 20 mg/kg S-duloxetine (its hydrochloride salt was used in the experiment). The test compound was I-1 (the compound I-1 prepared in Example 2 whose hydrochloride salt was used in the experiment), and the administration dosages were 5 mg/kg and 10 mg/kg. The drug was administrated by gavage based on the weight of mice. 1.5% acetic acid solution (0.1 ml/10 g) was injected intraperitoneally 1 h after administration, and the number of times of visceral pain in each group was observed within 30 min. When concave abdomen, stretched trunk and hind claw, and high buttocks appeared, one number point was recorded. Finally, the number of appearance of the above phenomenon was counted within 30 minutes. After administration, the fewer visceral pains in the mice were, the stronger the analgesic effect of the compound was.

Experimental Result

Figure 5:
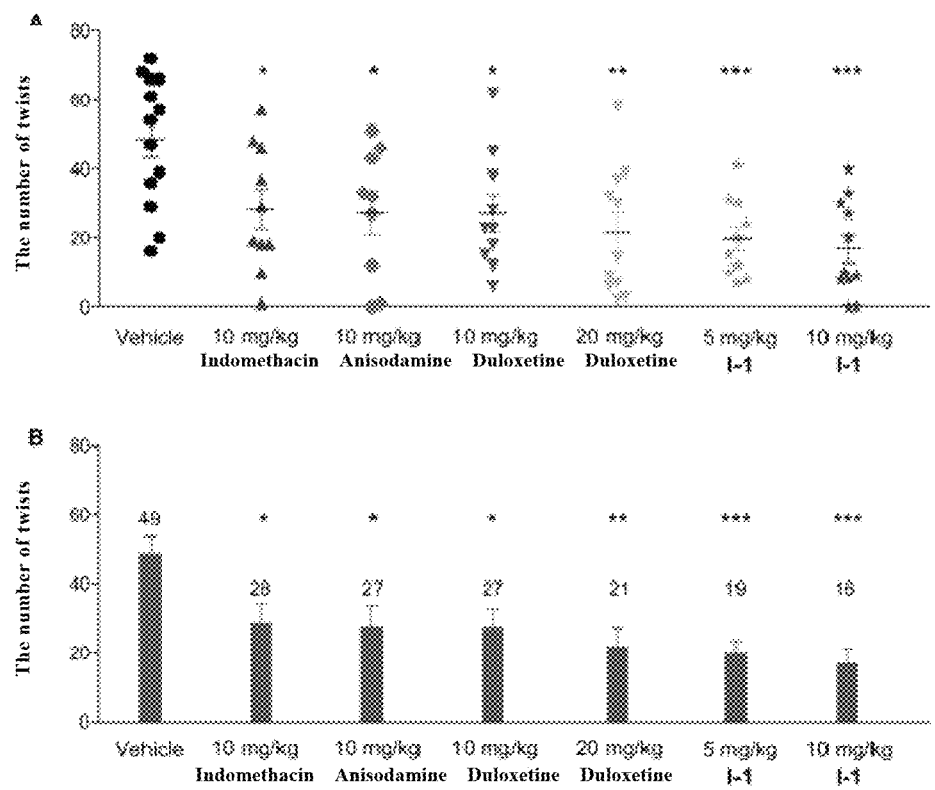
FIG. 5 shows the results of analgesic activity of compound I-1 of the present invention, S-duloxetine, indomethacin and anisodamine in the mouse acetic writhing pain model.

The mice acetic acid writhing pain model test was shown in FIG. 5. FIG. 5 showed that the compound I-1 (5 mg/kg and 10 mg/kg) of the present invention could significantly decreased the number of appearance of writhing reactions in mice caused by acetic acid in single intragastric administration. There was significant difference in the number of appearance of writhing reactions in mice compared with the saline group (vehicle, blank control) (49 times). At a dosage of 5 mg/kg of compound I-1, the number of appearance of visceral pain in mice was 19 times, which was 50% lower than the 49 times in the saline control group, suggesting that the half effective dose ($ED_{50}$) of compound I-1 was less than 5 mg/kg in the model. The analgesic effect of compound I-1 at a dose of 10 mg/kg (16 times) was stronger than that of positive drug indomethacin (28 times), anisodamine (27 times) and S-duloxetine (27 times) at the same dosage. The analgesic effect of compound I-1 at a dosage of 5 mg/kg (19 times) was equivalent to that of S-duloxetine at a dosage of 20 mg/kg (21 times). This experiment showed that the analgesic activity of compound I-1 of the present invention was significantly stronger than positive control drug in the mice acetic acid writhing pain model. The mice acetic acid writhing pain model was a classical model for evaluating the efficacy of drug in treating visceral pain and inflammatory pain. Therefore, compound I-1 of the present invention had excellent therapeutic effect on visceral pain and inflammatory pain.

Example 19

Evaluation of Therapeutic Effect of Compound I-1 on Nerve Pain in Rat SNL Model

Experimental Method

1. Animals Surgery

Male SPF grade SD rats, weighed 150 g-180 g, were selected. Aseptic operation during surgery was performed. The animals were anesthetized with sodium pentobarbital (50 mg/kg, intraperitoneal injection). The surgical area of animal waist was shaved and the skin was disinfected three times with iodophor and 70% ethanol. After the skin was dried, the operation was started. Surgical knife was used to make a longitudinal incision at the back of the sacrum of the animal waist to expose the left paraspinal muscles, and stretcher was used to separate muscle tissue to expose the spine. The left spinal nerves L5 and L6 were separated and ligated with a 6-0 silk thread, and the wound was sutured. After the operation, the animals were placed on electrothermal pad, and 5 mL of saline was injected subcutaneously to prevent dehydration. After the animals were fully awakened and could move around freely, the animals were put back in the cage.

2. Grouping and Mechanical Allodynia Test

After the operation, the animals were adapted in the experimental environment for 15 min/day for 3 days. One day before the administration, the rats were subjected to mechanical allodynia baseline test, and the animals that did not exhibit mechanical allodynia (the withdrawal threshold was greater than 5 g) were removed and the remaining rats were randomly divided into one control group and 3 experimental groups.

Administration

The animals were weighed to calculate the dose. The rats in 3 experimental groups were administrated with 100 mg/kg gabapentin, 10 mg/kg S-duloxetine (its hydrochloride salt was used in the experiment) and 10 mg/kg compound I-1 (the compound I-1 prepared in Example 2 whose hydrochloride salt was used in the experiment), the rats in control group were administrated with equal volume of normal saline orally. After administration, mechanical allodynia test was performed. The rat was individually placed in a plexiglass box with a grid on the bottom of the box to ensure that the rat claw could be tested. The rats were allowed to adapt the environment for 15 min before test. After the adaptation was completed, the test fiber was used to test the center of the left hind claw of the rat. The test fiber comprises 8 test strengths: 3.61 (0.4 g), 3.84 (0.6 g), 4.08 (1 g), 4.31 (2 g), 4.56 (4 g), 4.74 (6 g), 4.93 (8 g), and 5.18 (15 g). During the test, the test fiber was pressed vertically against the skin and forced to bend the fiber for 6-8 s with a 5 s interval of test. During the test, rapid withdrawal of animal claw was recorded as pain response. When the test fiber was removed from animal skin, the withdrawal of animal claw was also recorded as pain response. If animal moved, the pain response was not recorded, and the test was repeated. In the test, 4.31 (2 g) was used firstly. If animal responded to pain, the test fiber with lower strength was used in next test; if the animal did not respond to pain, test fiber with higher strength was used in next test. The maximum strength of tested fiber was 5.18 (15 g).

Mechanical allodynia was expressed as withdrawal threshold (PWT) in rat behavioral test, which was calculated with the following formula:

50% response threshold (g)=$(10^{(Xf+k\delta)})/10{,}000$;

Xf=the final test fiber value used in the test;
k=table value;
δ=mean difference Excel software was used to collect data, Prism 6.01 (Graph pad software, Inc.) software was used to analyze data. The larger the withdrawal threshold (PWT) was, the stronger the analgesic effect of the compound was.

Experimental Results

Figure 6:
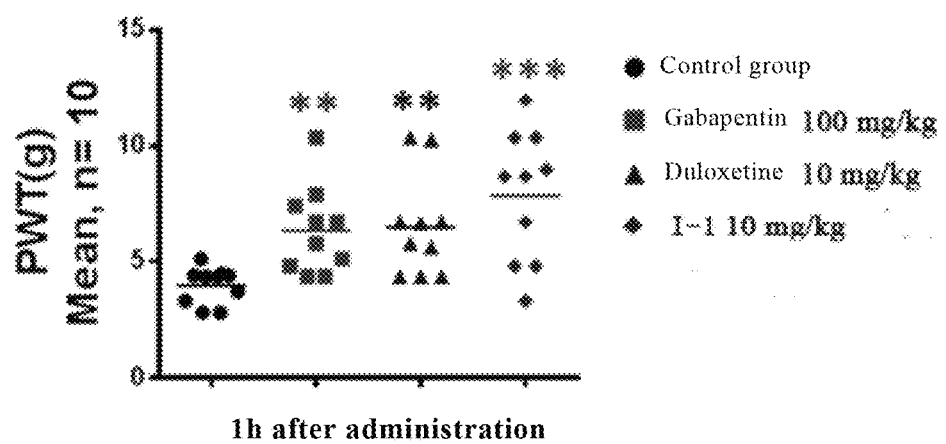
FIG. 6 shows the results of analgesic activity of compound I-1 of the present invention, S-duloxetine and gabapentin in the rat SNL model.

The results of analgesic activity in the rat SNL model were shown in Table 5 and FIG. 6. Table 5 and FIG. 6 showed that compared with the saline control group, compound I-1 of the present invention had very potent analgesic effect at a dosage of 10 mg/kg with a significant difference. Compared with the positive control group, the analgesic activity of compound I-1 of the present invention was stronger than the analgesic effects of 100 mg/kg gabapentin and 10 mg/kg of S-duloxetine within 1 h after administration. The rat SNL model was a classical model for evaluating the efficacy of drug in the treatment of nerve pain. Therefore, compound I-1 of the present invention had excellent therapeutic effect on nerve pain.

TABLE 5

The statistical data of claw withdrawal threshold (PWT) 1 h after administration of the compound I-1, S-duloxetine and gabapentin in the rat SNL model

| Compound | Dose | PWT(g) |
| --- | --- | --- |
| Control group |  | 3.967 ± 0.775 |
| Compound I-1 | 10 mg/kg | 7.869 ± 2.846 |
| S-duloxetine | 10 mg/kg | 6.519 ± 2.226 |
| Gabapentin | 100 mg/kg | 6.352 ± 1.897 |

All documents mentioned in the present invention are incorporated herein by reference, as if each document is individually cited for reference. It should be understood that those skilled in the art will be able to make various changes or modifications to the present invention after reading the teachings of the present invention, which also fall within the scope of the claims appended hereto.

The invention claimed is:

1. A compound, or a pharmaceutically acceptable salt thereof as a TRPA1 inhibitor, wherein the compound has a structure of formula Z:

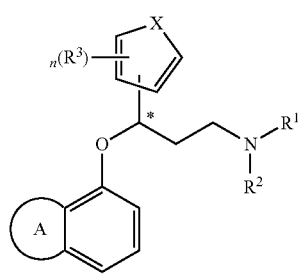

wherein, ring A is a furan ring;

the configuration of phenyl fused with ring A is

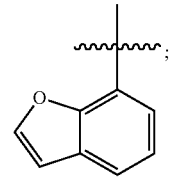 [SMILES: *c1cccc2ccoc12]

$R^1$ and $R^2$ are each independently hydrogen, substituted or unsubstituted $C_1$-$C_6$ alkyl, or substituted or unsubstituted $C_3$ cycloalkyl;

X is an oxygen atom or sulfur;

$R^3$ is hydrogen, halogen, $C_1$-$C_6$ alkyl, or $C_3$ cycloalkyl;

n is 1, 2 or 3;

"*" means that the configuration of the compound is racemate;

wherein any of the "substituted" means that 1-4 hydrogen atoms on the group are each independently substituted by a substituent selected from the group consisting of $C_1$-$C_6$ alkyl, $C_1$-$C_3$ haloalkyl, halogen, $C_1$-$C_6$ alkoxyl, or $C_1$-$C_6$ haloalkoxy.

2. The compound of claim 1, wherein the compound is selected from the following group:

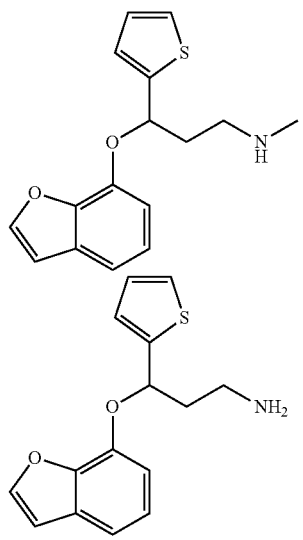

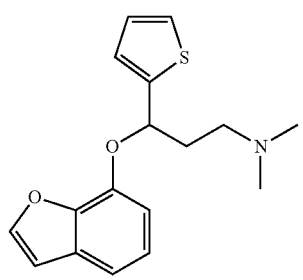

-continued

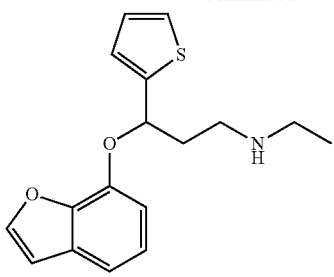

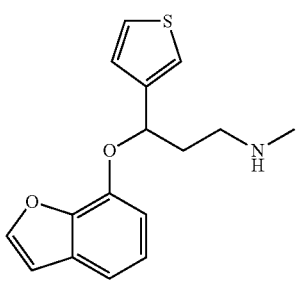

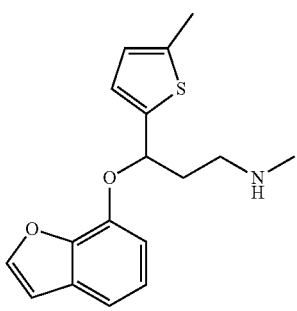

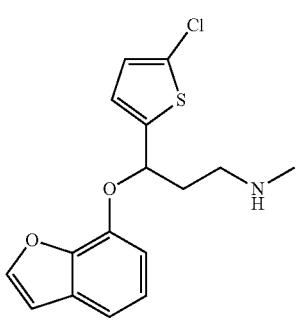

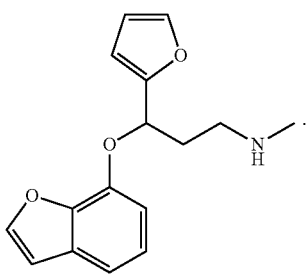

3. A compound, or a pharmaceutically acceptable salt thereof as a TRPA1 inhibitor, wherein the compound has a structure of formula I:

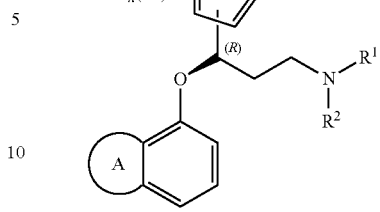

wherein,
ring A is a furan ring;
the configuration of phenyl fused with ring A is

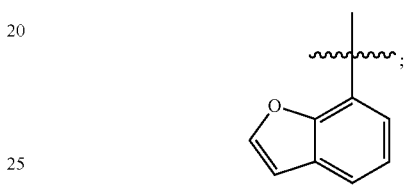

$R^1$ and $R^2$ are each independently hydrogen, substituted or unsubstituted $C_1$-$C_6$ alkyl, or substituted or unsubstituted $C_3$ cycloalkyl;
X is an oxygen atom or sulfur atom;
$R^3$ is hydrogen, halogen, $C_1$-$C_6$ alkyl, or $C_3$ cycloalkyl;
n is 1, 2 or 3;
wherein any of the "substituted" means that 1-4 hydrogen atoms on the group are each independently substituted by a substituent selected from the group consisting of $C_1$-$C_6$ alkyl, $C_1$-$C_3$ haloalkyl, halogen, $C_1$-$C_6$ alkoxyl, or $C_1$-$C_6$ haloalkoxy.

4. The compound of claim 3, wherein
$R^1$ and $R^2$ are each independently hydrogen or $C_1$-$C_3$ alkyl; and/or
$R^3$ is hydrogen, halogen, or $C_1$-$C_6$ alkyl.

5. The compound of claim 3,
X is S;
$R^1$ and $R^2$ are each independently hydrogen, methyl or ethyl;
$R^3$ is hydrogen atom, chlorine or a methyl; and/or
n is 1.

6. The compound of claim 3, wherein the compound is selected from the following group:

I-1

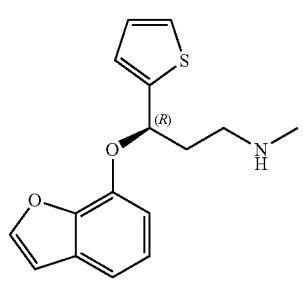

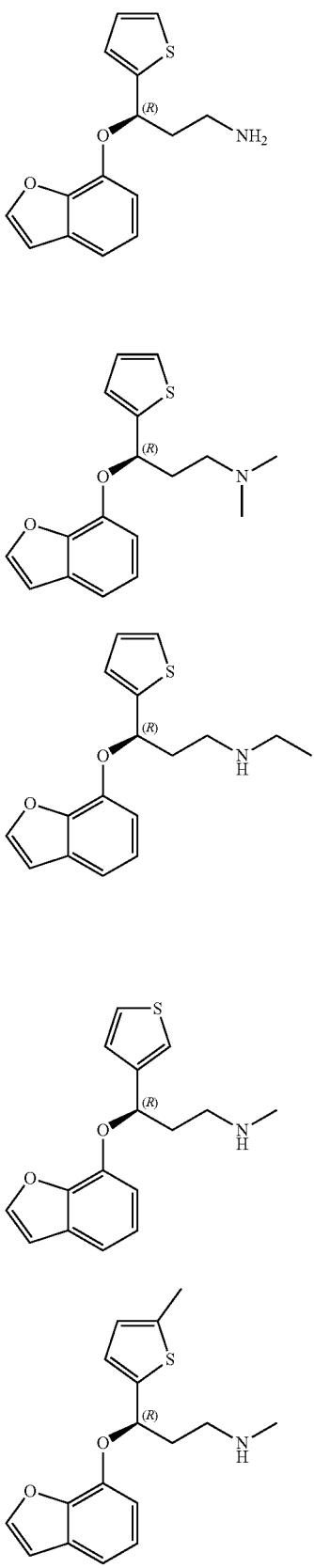

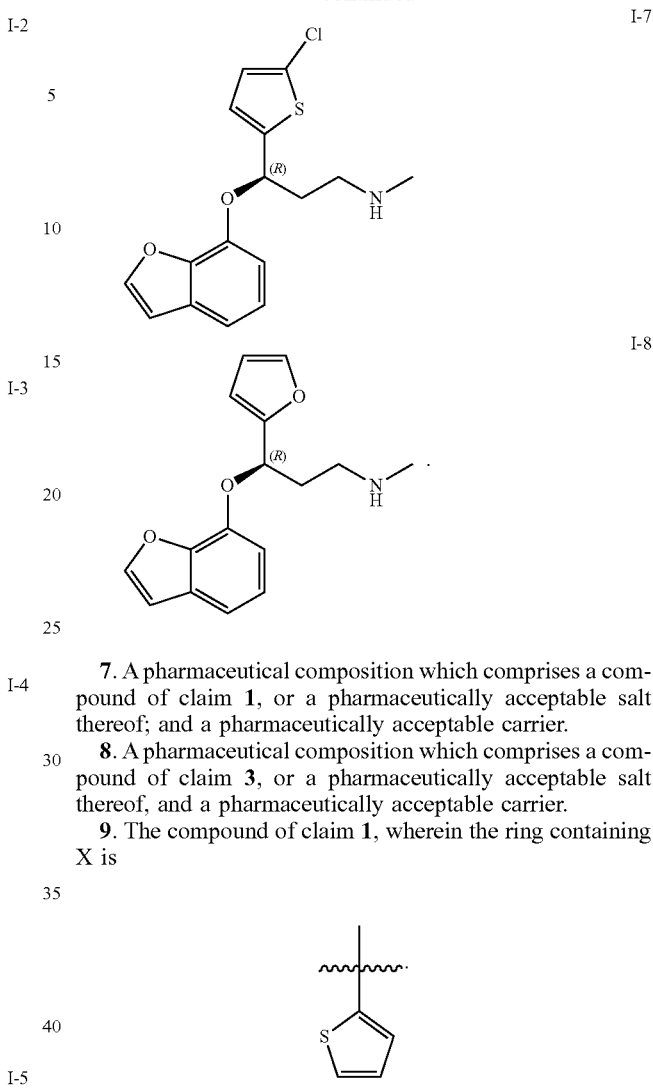

7. A pharmaceutical composition which comprises a compound of claim 1, or a pharmaceutically acceptable salt thereof; and a pharmaceutically acceptable carrier.

8. A pharmaceutical composition which comprises a compound of claim 3, or a pharmaceutically acceptable salt thereof, and a pharmaceutically acceptable carrier.

9. The compound of claim 1, wherein the ring containing X is

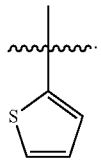 [SMILES: *c1cccs1]

10. The compound of claim 1, wherein,
$R^1$ and $R^2$ are each independently hydrogen or $C_1$-$C_3$ alkyl; and
$R^3$ is hydrogen, halogen, or $C_1$-$C_6$ alkyl.

11. The compound of claim 1,
X is S;
$R^1$ and $R^2$ are each independently hydrogen, methyl or ethyl;
$R^3$ is hydrogen atom, chlorine or a methyl; and/or
n is 1.

12. The compound of claim 3, wherein the ring containing X is

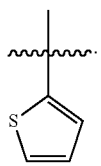 [SMILES: *c1cccs1]

* * * * *